United States Patent
Ideguchi et al.

(10) Patent No.: US 10,379,042 B2
(45) Date of Patent: Aug. 13, 2019

(54) FOURIER TRANSFORM-TYPE SPECTROSCOPIC DEVICE

(71) Applicant: The University of Tokyo, Tokyo (JP)

(72) Inventors: Takuro Ideguchi, Tokyo (JP); Kazuki Hashimoto, Tokyo (JP); Megumi Takahashi, Tokyo (JP); Yusuke Sakaki, Tokyo (JP); Keisuke Goda, Tokyo (JP)

(73) Assignee: The University of Tokyo, Tokyo (JP)

( * ) Notice: Subject to any disclaimer, the term of this patent is extended or adjusted under 35 U.S.C. 154(b) by 0 days.

(21) Appl. No.: 16/068,630

(22) PCT Filed: Dec. 28, 2016

(86) PCT No.: PCT/JP2016/089069
§ 371 (c)(1),
(2) Date: Jul. 6, 2018

(87) PCT Pub. No.: WO2017/119389
PCT Pub. Date: Jul. 13, 2017

(65) Prior Publication Data
US 2018/0321143 A1 Nov. 8, 2018

(30) Foreign Application Priority Data

Jan. 8, 2016 (JP) .................................. 2016-002975

(51) Int. Cl.
*G01N 21/65* (2006.01)
*G01N 21/3586* (2014.01)
(Continued)

(52) U.S. Cl.
CPC ..... *G01N 21/3586* (2013.01); *G01B 11/2441* (2013.01); *G01J 3/44* (2013.01);
(Continued)

(58) Field of Classification Search
CPC ..... G02B 26/12; G01J 3/45; G01J 3/44; G01J 3/2889; G01J 2003/451; G01N 21/65
See application file for complete search history.

(56) References Cited

U.S. PATENT DOCUMENTS 7,751,057 B2 * 7/2010 Oldenburg ........... A61B 5/0066
356/497
7,889,348 B2 * 2/2011 Tearney ................. A61B 1/043
356/451
(Continued)

FOREIGN PATENT DOCUMENTS

JP      H0712648 A      1/1995
JP      2001527659 A      12/2001
(Continued)

OTHER PUBLICATIONS

Kamali, et al: "Hybrid Single-Source Online Fourier Transform Coherent Anti-Stokes Raman Scattering/Optical Coherence Tomography", Optics Letters, Oct. 1, 2014, vol. 39, No. 19, pp. 5709-5712.
(Continued)

*Primary Examiner* — Maurice C Smith
(74) *Attorney, Agent, or Firm* — Fox Rothschild LLP; Robert J. Sacco; Carol E. Thorstad-Forsyth

(57) ABSTRACT

Provided is a Fourier transform-type spectroscopic device capable of improving an acquisition speed of a molecular vibration spectrum. The Fourier transform-type spectroscopic device (1) of the present invention rotates a scanning mirror (26b) by rotation of a rotating shaft (26a) to change a light path length of scanning light and delay or advance the scanning light with respect to reference light in accordance with a rotation angle of the scanning mirror (26b) from an initial position, and is thus capable of moving the scanning mirror (26b) at a high speed as compared with a case where a movable mirror is mechanically moved as in a conven-
(Continued)

tional Fourier transform-type spectroscopic device, thereby improving an acquisition speed of a molecular vibration spectrum.

8 Claims, 11 Drawing Sheets

(51) Int. Cl.
| | |
|---|---|
| *G01J 3/45* | (2006.01) |
| *G02B 5/18* | (2006.01) |
| *G02B 26/10* | (2006.01) |
| *G02B 26/12* | (2006.01) |
| *G01B 11/24* | (2006.01) |
| *G01N 21/3563* | (2014.01) |
| *G01N 21/47* | (2006.01) |
| *G02B 27/42* | (2006.01) |
| *G01J 3/44* | (2006.01) |

(52) U.S. Cl.
CPC ............ *G01J 3/45* (2013.01); *G01N 21/3563* (2013.01); *G01N 21/4795* (2013.01); *G01N 21/65* (2013.01); *G02B 5/18* (2013.01); *G02B 5/1828* (2013.01); *G02B 26/10* (2013.01); *G02B 26/12* (2013.01); *G02B 27/4244* (2013.01); *G01N 2021/653* (2013.01)

(56) References Cited

U.S. PATENT DOCUMENTS

| | | | |
|---|---|---|---|
| 8,175,685 B2* | 5/2012 | Yun | A61B 3/102 356/479 |
| 2003/0137669 A1 | 7/2003 | Rollins et al. | |
| 2009/0206263 A1* | 8/2009 | Rahman | G01J 3/02 250/341.1 |
| 2016/0076940 A1* | 3/2016 | Kimura | G01N 21/65 356/301 |

FOREIGN PATENT DOCUMENTS

| | | |
|---|---|---|
| JP | 2006215006 A | 8/2006 |
| JP | 2007240453 A | 9/2007 |
| JP | 2011527418 A | 10/2011 |
| JP | 2013040849 A | 2/2013 |
| JP | 2015534482 A | 12/2015 |
| WO | 2006092874 A1 | 9/2006 |
| WO | 20150198846 A1 | 12/2015 |

OTHER PUBLICATIONS

Ogilvie, et al: "Fourier-Transform Coherent Anti-Stokes Raman Scattering Microscopy", Optics Letters, Feb. 15, 2006, vol. 31, No. 4, pp. 480-482.

* cited by examiner

FOURIER TRANSFORM-TYPE SPECTROSCOPIC DEVICE

TECHNICAL FIELD

The present invention relates to a Fourier transform-type spectroscopic device.

BACKGROUND ART

As a technique for measuring a molecular vibration spectrum of a sample, Fourier-transform spectroscopy is known, such as Fourier-transform infrared spectroscopy (also referred to as FT-IR) (cf. Patent Literature 1) and Fourier-transform coherent anti-Stokes Raman scattering (also referred to as FT-CARS) spectroscopy (cf. Non Patent Literature 1).

In the Fourier-transform spectroscopy, an interference wave is produced using a Michelson interferometer in which light emitted from a light source is split by a beam splitter into reference light which propagates in a first arm including a fixed mirror and scanning light which propagates in a second arm including a movable mirror, and the reference light reflected on the fixed mirror of the first arm is combined with the scanning light reflected on the movable mirror of the second arm, and the sample is then irradiated with the produced interference wave.

In the Fourier-transform spectroscopy, in the Michelson interferometer, the movable mirror is moved in one direction to change a light path length of the second arm and delay the scanning light with respect to the reference light, thereby producing an interferogram of an interference wave, and a Fourier transform of the interferogram is performed to obtain a molecular vibration spectrum.

In the FT-IR, an interferogram of transmitted light, generated by transmission of an interference wave through a sample, is produced and a Fourier transform of the interferogram is performed, to obtain a molecular vibration spectrum of the sample.

In the FT-CARS spectroscopy, an interferogram of anti-Stokes light, emitted due to coherent anti-Stokes Raman scattering which has occurred in a sample by irradiation with an interference wave, is produced and a Fourier transform of the interferogram is performed to obtain a molecular vibration spectrum of the sample.

As thus described, in the Fourier-transform spectroscopy, an interferogram is produced by delaying the scanning light with respect to the reference light by using the Michelson interferometer, and a Fourier transform of the interferogram is performed to obtain a molecular vibration spectrum.

CITATION LIST

Patent Literature

Patent Literature 1: Japanese Patent Laid-Open No. 7-12648

Non Patent Literature

Non Patent Literature 1: Jennifer P. Ogilvie et al., OPTICS LETTERS/Vol. 31, No. 4, 480 (2006)

SUMMARY OF INVENTION

Technical Problem

However, the Fourier-transform spectroscopy has had a problem as follows: because an interferogram is produced in the Michelson interferometer by moving the position of the movable mirror to change a difference in the light path length between the first arm and the second arm during measurement, a production speed of an interferogram is limited by a moving speed of the movable mirror, thus making it hard to improve an acquisition speed of a molecular vibration spectrum.

Therefore, an object of the present invention is to provide a Fourier transform-type spectroscopic device capable of improving an acquisition speed of a molecular vibration spectrum.

Solution to Problem

A Fourier transform-type spectroscopic device of the present invention is provided with: an interferometer that includes a beam splitter which is configured to splits light emitted from a light source into reference light and scanning light, a first arm which is configured to cause the reference light to be reflected on a first mirror and incident again on the beam splitter, and a second arm which is configured to cause the scanning light to be reflected on a second mirror and incident again on the beam splitter, the interferometer configured to combine the reference light and the scanning light incident again on the beam splitter, to produce an interference wave; a photodetector that is configured to detect intensity of light to be detected, emitted from a sample irradiated with the interference wave; and an optical spectrum production unit that is configured to produce an interferogram based on intensity of a plurality of the light to be detected, obtained by repeated irradiation of the sample with the interference wave, and is configured to perform a Fourier transform of the interferogram, wherein the second arm includes a scanning mirror disposed on a light path of the scanning light between the beam splitter and the second mirror, and is configured to delay or advance the scanning light with respect to the reference light in accordance with a rotation angle of the scanning mirror from an initial position.

Advantageous Effects of Invention

The Fourier transform-type spectroscopic device of the present invention rotates a scanning mirror to change a light path length of scanning light and delay or advance the scanning light with respect to reference light in accordance with a rotation angle of the scanning mirror from an initial position, and is thus capable of moving the scanning mirror at a high speed as compared with a case where a position of a movable mirror to delay the scanning light with respect to the reference light as in a conventional Fourier transform-type spectroscopic device, thereby improving an acquisition speed of a molecular vibration spectrum.

BRIEF DESCRIPTION OF DRAWINGS

FIG. 10 is an explanatory view showing a measuring state at the time of taking beads each flowing in a micro flow path as a measuring object by using the Fourier transform-type spectroscopic device according to the embodiment of the present invention, where

DESCRIPTION OF EMBODIMENTS

The embodiment of the present invention will be described with reference to the drawings.

Figure 1:
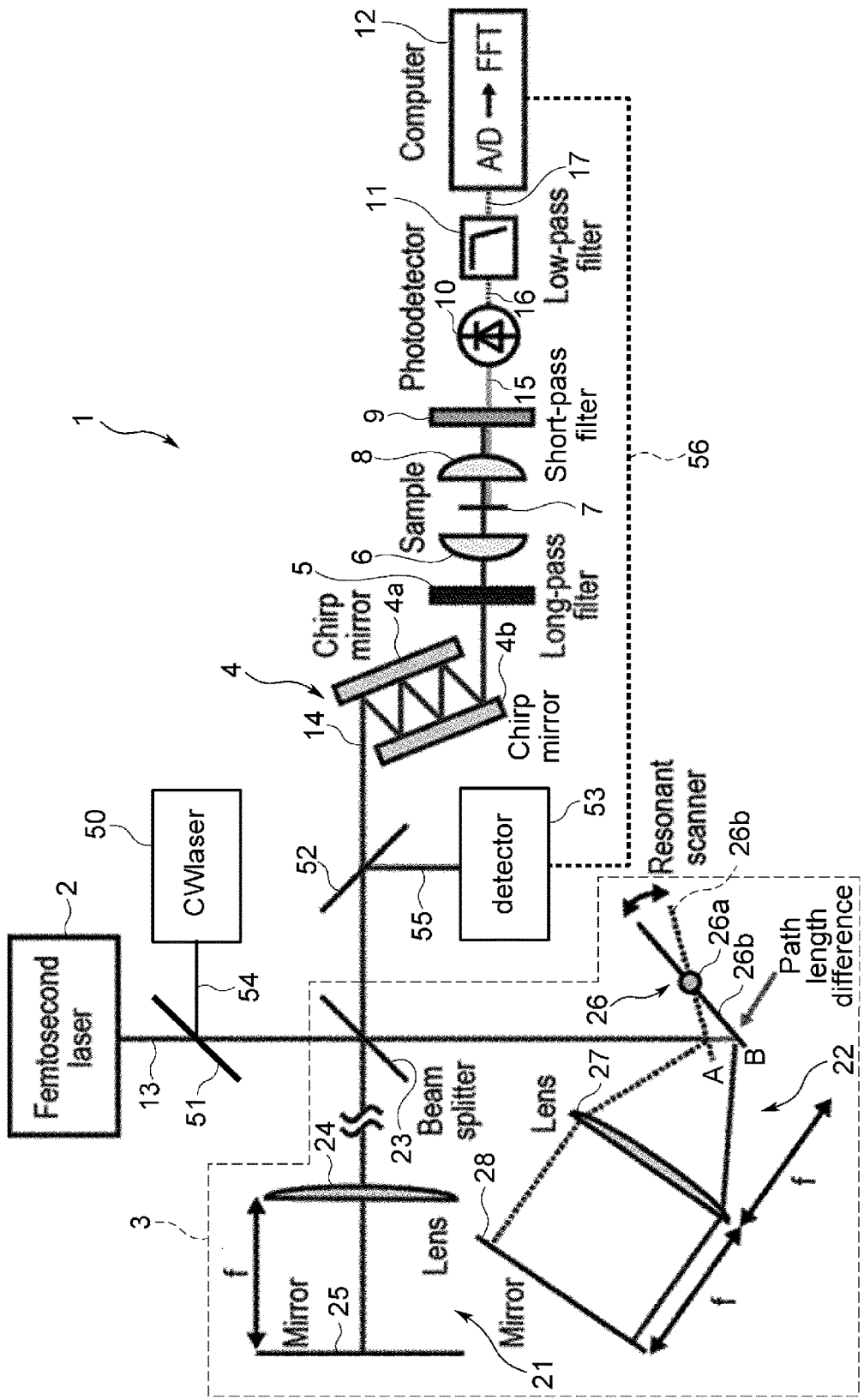
FIG. 1 is a schematic diagram showing an entire configuration of a Fourier transform-type spectroscopic device according to an embodiment of the present invention.

(1) Entire Configuration of Fourier Transform-Type Spectroscopic Device According to Embodiment of the Present Invention As shown in FIG. 1, a Fourier transform-type spectroscopic device 1 according to an embodiment of the present invention is provided with a light source 2, an interferometer 3, a compensator 4, a long pass filter 5, a first objective lens 6, a second objective lens 8, a short pass filter 9, a photodetector 10, a low-pass filter 11, and a personal computer (hereinafter referred to as PC) 12 as an optical spectrum production unit.

The Fourier transform-type spectroscopic device 1 is a Fourier-transform coherent anti-Stokes Raman scattering (FT-CARS) spectroscopic device that produces an interferogram of anti-Stokes light 15 as light to be detected, emitted due to coherent anti-Stokes Raman scattering which has occurred in the sample 7 by irradiation with an interference wave 14 produced in the interferometer 3, by using the interferometer 3 and performs a Fourier transform of the interferogram with the PC 12, to obtain a molecular vibration spectrum.

In the present embodiment, the light source 2 is a laser light source that emits ultrashort-pulse laser light with high coherency and is a pulse laser that emits a light pulse 13 having a broadband spectrum at a predetermined repetition frequency. Specifically, the light source 2 is a Ti-sapphire femtosecond laser (manufactured by Femtolasers, Inc., product name: Synergy (registered trade mark)) that emits the light pulse 13 with a center frequency of 792 nm, a band width of 47 nm, and a pulse width of 17 fs at a repetition frequency of 75 MHz. As the light source 2, various types of pulse lasers (a solid-state laser, a fiber laser, a dye laser, etc.) with high repetition frequencies are usable.

The interferometer 3 is provided with: a beam splitter 23; a first arm 21 including a dispersion lens 24 and a first mirror 25; and a second arm 22 including a resonant scanner 26, a collector lens 27, and a second mirror 28. The interferometer 3 is a Michelson interferometer that splits the light pulse 13 emitted from the light source 2 into reference light which propagates in the first arm 21 and scanning light which propagates in the second arm 22 in the beam splitter 23, makes the reference light, reflected on the first mirror 25 of the first arm 21, and the scanning light, reflected on the second mirror 28 of the second arm 22, incident again on the beam splitter 23, and combines the reference light and the scanning light incident again on the beam splitter 23, to produce the interference wave 14. The reference light and the scanning light split in the beam splitter 23 are both a light pulse similar to the light pulse 13. In the present embodiment, a polarization independent beam splitter BSW26R (25×36 mm, 50:50, UVFS plate type beam splitter, coating: 350 to 1100 nm, t=1 mm) manufactured by Thorlabs, Inc. is used as the beam splitter 23. In addition to such a polarization independent beam splitter, a polarization beam splitter is also usable as the beam splitter 23.

The first arm 21 is configured such that the dispersion lens 24 is provided on a light path between the beam splitter 23 and the first mirror 25 and the reference light is transmitted through the dispersion lens 24 and incident on the first mirror 25. The dispersion lens 24 is disposed at a distance from the first mirror 25 which is the same as a focal distance f of the dispersion lens 24.

The dispersion lens 24 is a similar lens to the collector lens 27 of the second arm 22 described later. The dispersion lens 24 causes occurrence of group velocity dispersion in the reference light, which is similar to group velocity dispersion having occurred in the scanning light by transmission of the scanning light through the collector lens 27. In this manner, the dispersion lens 24 is disposed to cause occurrence of the group velocity dispersion in the reference light, which is similar to the group velocity dispersion that occurs in the scanning light, so that pulse shapes of the reference light and the scanning light can be made uniform and the intensity of anti-Stokes light described later can be enhanced, to obtain a molecular vibration spectrum with high sensitivity. Note that the first arm 21 preferably includes the dispersion lens 24 but may include no dispersion lens.

The first mirror 25 is a plane mirror and disposed vertically to the light beam of the reference light. Hence the reference light is vertically incident on the mirror surface of the first mirror 25 and reflected thereon, and the reflected reference light is vertically emitted from the mirror surface and passes along the same path as at the time of incidence in a reverse direction. Therefore, in the first arm 21, when the reference light split in the beam splitter 23 is reflected on the first mirror 25, the reflected light passes along the same path in the reverse direction and is incident again on the beam splitter 23.

The second arm 22 is configured such that the scanning light split in the beam splitter 23 is reflected on a scanning mirror 26b of the resonant scanner 26, and the reflected light is transmitted through the collector lens 27 and incident on the second mirror 28.

In the resonant scanner 26, the scanning mirror 26b is attached to one end of a rotating shaft 26a, the rotating shaft 26a is rotated by a rotation control unit (not shown in FIG. 1) connected to the other end of the rotating shaft 26a, and the scanning mirror 26b resonantly vibrates by rotation of the rotating shaft 26a. As a result, the scanning mirror 26b performs periodic motion at a predetermined deflection angle. In the present embodiment, as the resonant scanner 26, a CRS manufactured by Cambridge Technology is used, with which the scanning mirror 26b vibrates at 8 kHz. As the resonant scanner 26, another form of the resonant scanner may be used.

While the vibration frequency of the scanning mirror 26b can be selected as appropriate in accordance with parameters (repetition frequency, pulse width, etc.) of the light pulse 13 to be used, a preferable frequency is about 10 kHz. When the light source 2 is used which emits the light pulse 13 with a pulse width of 17 fs at a repetition frequency of 75 MHz as in the above embodiment, a molecular vibration spectrum is also measurable by using the resonant scanner 26 including the scanning mirror 26b that vibrates at about a vibration frequency of 76 kHz.

In the second arm 22, the resonant scanner 26 is disposed such that, during resonant vibration of the scanning mirror 26b, the scanning light split in the beam splitter 23 is constantly applied to a portion of the scanning mirror 26b which is greatly displaced due to the resonant vibration, that is the vicinity of the outer edge of the scanning mirror 26b here. The scanning mirror 26b of the resonant scanner 26 is disposed on the light path of the scanning light, and is disposed so as to be displaced to a position farthest from the beam splitter 23 (a position B of the scanning mirror 26b indicated by a solid line shown in FIG. 1) due to resonant vibration generated by rotation of the rotating shaft 26a, with a position that is closest to the beam splitter 23 (a position A of the scanning mirror 26b indicated by a broken line shown in FIG. 1) taken as an initial position, and then returns to the initial position. As thus described, the scanning mirror 26b performs periodic motion between the position A and the position B.

Hence in the second arm 22, the distance between the beam splitter 23 and the scanning mirror 26b changes in accordance with the rotation angle of the scanning mirror 26b from the initial position due to periodic motion, resulting in a change in the light path of the scanning light. Here, the rotation angle is the rotation angle of the rotating shaft 26a at the time when the scanning mirror 26b rotates. When the scanning mirror 26b reaches the position B, the rotation angle of the scanning mirror 26b becomes maximal and the light path of the scanning light becomes maximal. Thereafter, the rotating shaft 26a rotates reversely, the light path of the scanning light becomes shorter as the rotation angle of the scanning mirror 26b becomes smaller, and the scanning mirror 26b returns to the position A which is the initial position. In this manner, the light path length of the scanning light periodically changes in the second arm 22. In the case of the present embodiment, when the position of the scanning mirror 26b changes between the position A and the position B, a width of change in the light path length of the scanning light is about 1 mm. By changing the position at which the scanning mirror 26b is irradiated with the scanning light, the width of change in the light path length can be adjusted. In the second arm 22, the scanning mirror 26b is resonantly vibrating at a frequency of 8 kHz and thus performs periodic motion to reciprocate between the position A and the position B with a period of 125 µs.

The scanning mirror 26b of the resonant scanner 26 and the collector lens 27, as well as the collector lens 27 and the second mirror 28, are separated from each other at the same distance as a focal distance f of the collector lens 27, and the scanning mirror 26b, the collector lens 27, and the second mirror 28 form a so-called 4f optical system. The collector lens 27 refracts the incident scanning light to collect the scanning light on the mirror surface of the second mirror 28 being a plane mirror and make the collected light vertically incident on the mirror surface, and refracts the scanning light, reflected on the second mirror 28 and incident again thereon, to collect the scanning light on the scanning mirror 26b.

The angle formed by the scanning mirror 26b and the light beam of the scanning light changes in accordance with the rotation angle of the scanning mirror 26b, and the direction in which the scanning light is reflected on the scanning mirror 26b also changes. For this reason, the sizes of the collector lens 27 and the second mirror 28 are selected and the positions thereof are adjusted such that the scanning light is vertically incident on the second mirror 28 irrespective of the rotation angle of the scanning mirror 26b.

The scanning light is vertically incident on the second mirror 28 and reflected thereon, and the scanning light is thus emitted vertically from the second mirror 28 and passes along the same path as at the time of incidence in the reverse direction. Therefore, in the second arm 22, when the scanning light is reflected on the second mirror 28, the scanning light passes along the same path in the reverse direction and is incident again on the beam splitter 23. In the case of the present embodiment, the collector lens 27 (dispersion lens 24) is a circular spherical lens with a focal distance of 100 mm and a diameter of 2 inches. Each of the first mirror 25 and the second mirror 28 is a circular mirror with a diameter of 2 inches.

The reference light reflected on the first mirror 25 and the scanning light reflected on the second mirror 28 are incident again on the beam splitter 23 and interfere with each other to become the interference wave 14. In the interferometer 3, the placement of the constituent elements of the first arm 21 and the second arm 22 is adjusted such that the light path length of the reference light of the first arm 21 (the light path length of the reference light in reciprocation between the beam splitter 23 and the first mirror 25) is the same as the light path length of the scanning light of the second arm 22 (the light path length of the scanning light in reciprocation between the beam splitter 23 and the second mirror 28) at the time when the scanning mirror 26b of the resonant scanner 26 is at the initial position.

For this reason, when the scanning mirror 26b is at the initial position, the scanning light which propagates in the second arm 22 reaches the beam splitter 23 without a delay with respect to the reference light which propagates in the first arm 21, and because the reference light and the scanning light are the light split from the same light pulse 13, the reference light and the scanning light are superimposed to strengthen each other and produce the interference wave 14.

In contrast, when the rotation angle of the scanning mirror 26b of the resonant scanner 26 increases, the light path length of the scanning light of the second arm 22 increases, and the scanning light comes to reach the beam splitter 23 with a delay with respect to the reference light. At this time, the interference wave 14 becomes a collinear light pulse obtained by alignment of the reference light and the delayed scanning light on the same light axis and superimposition of the scanning light in the delayed state on the reference light.

In accordance with the rotation angle of the scanning mirror 26b, the light path length of the scanning light becomes longer and the difference in the light path length between the reference light and the scanning light becomes larger, so that the delay in the scanning light with respect to the reference light increases in accordance with the rotation angle of the scanning mirror 26b. When the scanning mirror 26b reaches the position B and the rotation angle of the scanning mirror 26b becomes maximal, the difference in the light path length between the reference light and the scanning light becomes maximal and the delay in the scanning light with respect to the reference light becomes maximal.

Then, the rotating shaft 26a rotates in the reverse direction, the rotation angle of the scanning mirror 26b becomes smaller, the scanning mirror 26b moves from the position B toward the position A, the light path length of the scanning light becomes smaller, and the difference in the light path length between the reference light and the scanning light becomes smaller, so that the delay in the scanning light with respect to the reference light decreases. The scanning mirror 26b resonantly vibrates by rotation of the rotating shaft 26a and performs periodic motion between the position A and the position B, and hence such a process as above is repeated.

In this manner, the interferometer 3 produces the interference wave 14 in which the scanning light is delayed with respect to the reference light in accordance with the rotation angle of the scanning mirror 26b from the initial position.

The interference wave 14 is incident on the compensator 4. The compensator 4 is designed to compensate the group velocity dispersion of the interference wave 14 to minimize the pulse width of the interference wave 14 at the position of the sample 7, namely, at the time of irradiation of the sample 7 with the interference wave 14. In the case of the present embodiment, the compensator 4 is a so-called pair of chirped mirrors and made up of a first chirped mirror 4a and a second chirped mirror 4b in parallel to the first chirped mirror 4a. The first chirped mirror 4a and the second chirped mirror 4b are disposed such that the mirror surfaces thereof face each other, and the interference wave 14, incident on the compensator 4 from its one end propagates while being repeatedly reflected between the first chirped mirror 4a and the second chirped mirror 4b, and are then emitted from the other end of the compensator 4. The first chirped mirror 4a and the second chirped mirror 4b may be disposed at an interval of about several centimeters and are disposed at an interval of about 2 cm in the case of the present embodiment.

The group velocity dispersion of the interference wave 14 is compensated each time the interference wave 14 is reflected between the first chirped mirror 4a and the second chirped mirror 4b, and the pulse width thereof becomes narrower at the position of the sample 7. As thus described, the compensator 4 compensates the group velocity dispersion of the interference wave 14 to narrow the pulse width thereof. By the compensator 4 compensating the group velocity dispersion of the interference wave 14, it is possible to facilitate occurrence of Raman scattering in the sample 7 and more reliably obtain a molecular vibration spectrum. The compensator 4 is not particularly limited so long as being capable of compensating the group velocity dispersion of the interference wave 14 to narrow the pulse width, and it is possible to use another form of the element or the like which is capable of compensating the group velocity dispersion. For example, a pair of diffraction gratings, a photonic crystal fiber (PCF), a chirped fiber Bragg grating (chirped FBG), or the like may be used as the compensator 4. These elements including the pair of chirped mirrors compensate the group velocity dispersion, namely, compensate up to secondary dispersion, but it is preferable to use the compensator 4 that compensates up to a high-order (tertiary or higher-order) dispersion, such as a prism pair or a grism pair.

The interference wave 14, with its group velocity dispersion compensated in the compensator 4, passes through the long pass filter 5 and is collected on the first objective lens 6, and the sample 7 is then irradiated with the interference wave 14. A cutoff wavelength is set in the long pass filter 5 so as not to transmit light at the bottom on the short wavelength side in the spectrum of the interference wave 14. This enables the long pass filter 5 to cut off light with a wavelength being about the same as the wavelength of the anti-Stokes light 15 generated in the sample 7, which will be described later, so that it is possible to facilitate detection of the anti-Stokes light 15 and more reliably obtain a molecular vibration spectrum. In the case of the present embodiment, in the long pass filter 5, the cutoff wavelength has been set to 750 mm.

The sample 7 is disposed at the focal position of the first objective lens 6. When the interference wave 14 is applied to the sample 7, first, the reference light is applied to the sample 7. Then, light with a certain frequency contained in the reference light becomes pump light, light with a certain frequency different from the pump light becomes Stokes light, and in the sample 7, molecular vibration is induced which has the same vibration frequency as a difference in frequency between the pump light and the Stokes light. Thereafter, when the scanning light being delayed with respect to the pulse of the reference light is applied to the sample 7, the scanning light and the induced molecular vibration act to shift the frequency of light contained in the scanning light, and scattered light is emitted. This scattered light contains the anti-Stokes light 15 with its frequency increased by the frequency of the molecular vibration induced by the reference light with respect to the frequency of the scanning light and contains the Stokes light with its frequency decreased by the frequency of the molecular vibration induced by the reference light with respect to the frequency of the scanning light.

The intensity of each of the anti-Stokes light 15 and the Stokes light emitted from the sample 7 changes in accordance with the time of delay in the scanning light with respect to the reference light, so that the time of delay is changed by the interferometer 3 to produce an interferogram of the anti-Stokes light 15 or the Stokes light, and a Fourier transform of the interferogram is then performed to enable a molecular vibration spectrum to be obtained.

With the reference light being a broadband light pulse and having wavelength components in a wide range, various sorts of molecular vibration are induced by combinations of pump light and Stokes light with various frequencies, to enable emission of the anti-Stokes light 15 and the anti-Stokes light corresponding to the various sorts of molecular vibration. Hence it is possible to obtain a molecular vibration spectrum in a wide wavenumber region by producing an interferogram once.

When the scanning light is advanced with respect to the reference light, first, the scanning light is applied to the sample 7 to induce molecular vibration. Then, the reference light is applied to the sample 7, and the anti-Stokes light 15 and the Stokes light are emitted. In this case, the time of advance of the scanning light is change by the interferometer 3 to change the time difference between the scanning light and the reference light and produce an interferogram of the anti-Stokes light 15 or the Stokes light.

The anti-Stokes light 15 and the Stokes light are together collimated with the interference wave 14, transmitted through the sample 7, on the second objective lens 8, the focal position of which superimposes with the focal position of the first objective lens 6 and which is dispose so as to face the first objective lens 6 with the focal position located therebetween, and the collimated light is incident on the short pass filter 9.

In the short pass filter 9, the cutoff wavelength has been set to a short wavelength equal to or shorter than the cutoff wavelength of the long pass filter 5. In the interference wave 14, most of wavelength components equal to or shorter than the cutoff wavelength of the long pass filter 5 have been cut off by the long pass filter 5, and there is thus a small number of wavelength components passable through the short pass filter 9. Further, the Stokes light is obtained by the frequency shift of light contained in the scanning light to the low frequency side, and hence the Stokes light has a larger number of wavelength components with long wavelengths than in the wavelength of the interference wave 14 formed by combination of the scanning light and the reference light, and thus has a small number of wavelength components passable through the short pass filter 9 similarly to the interference wave 14. Hence the short pass filter 9 can remove most of the interference wave 14 and the Stokes light. In the case of the present embodiment, the cutoff wavelength for the short pass filter 9 has been set to 750 mm.

The anti-Stokes light 15 having passed through the short pass filter 9 is detected in the photodetector 10, and the intensity of the anti-Stokes light 15 is converted into an electric signal. The electric signal of the intensity of the anti-Stokes light 15 passes through the low-pass filter 11 connected to the photodetector 10 through a conductive wire 16. In the low-pass filter 11, high-frequency noise is removed. The electric signal with its noise removed is transferred to the PC 12 connected to the low-pass filter 11 through a conductive wire 17. In the case of the present embodiment, an avalanche detector APD120A/M, manufactured by Thorlabs, Inc., has been used as the photodetector 10, but there is no limitation, and another form of the photodetector, such as a photomultiplier tube PIN photodiode, may be used.

A digitizer board is mounted in the PC 12 as the optical spectrum production unit, and the conductive wire 17 is connected to the digitizer board. The electric signal of the intensity of the anti-Stokes light 15, transferred from the low-pass filter 11, is converted from analog to digital by the digitizer board, and stored as electronic data into a storage (not shown in FIG. 1) of the PC 12 together with the detection time. In the present embodiment, ATS9440, manufactured by Alazar Technologies, Inc., is used as the digitizer board.

As described above, each time the light pulse 13 is produced in the light source 2, namely, with the repetition period of the light pulse 13, the detection time and the intensity of the anti-Stokes light 15 emitted from the sample 7 irradiated with the interference wave 14 are sequentially stored as electronic data. As a result, electronic data of an interferogram is produced in which values of the intensity of anti-Stokes light 15 are arranged at the same time intervals as the repetition period of the light pulse 13. In this manner, the interferogram of the anti-Stokes light 15 is produced based on the intensity of the anti-Stokes light 15. In the electronic data of the interferogram, the detection time and the intensity of the anti-Stokes light 15 are not necessarily stored each time the light pulse 13 is produced, and the detection interval for the anti-Stokes light 15 may be made longer to reduce the number of pieces of data as appropriate, or the detection interval may be made shorter to perform oversampling.

The scanning mirror 26b performs reciprocating motion between the initial position and the position B described above on the light path of the scanning light, and the speed of the scanning mirror 26b is almost constant in a region other than the vicinities of the initial position and the position B. As a result, it can be considered that in the region other than the vicinities of the initial position and the position B, an amount of change in the light path length of the scanning light per unit time is almost constant, the light path length of the scanning light changes in a temporally linear manner, and the delay in the scanning light with respect to the reference light also changes in a temporally linear manner.

In contrast, the speed of the scanning mirror 26b changes in the vicinities of the initial position and the position B. As a result, the amount of change in the light path length of the scanning light per unit time changes in accordance with the speed, and the light path length of the scanning light does not change in a temporally linear manner. The delay in the scanning light with respect to the reference light does not either change in a temporally linear manner.

The interferogram produced by the above method contains the intensity of the anti-Stokes light 15 detected in a time region in which the delay in the scanning light with respect to the reference light does not change in a temporally linear manner. For this reason, when a Fourier transform of the interferogram is performed to acquire a molecular vibration spectrum, distortion occurs in the acquired molecular vibration spectrum. In the present embodiment, the time axis is corrected such that the light path length of the scanning light changes in a temporally linear manner and the delay in the scanning light with respect to the reference light also changes in a temporally linear manner even in the vicinities of the initial position and the position B.

For making the above correction, the Fourier transform-type spectroscopic device 1 further includes: a light source 50 that emits continuous wave (CW) laser light 54; a beam splitter 51 that superimposes the CW laser light 54 on the same optical axis as the light pulse 13 and makes the CW laser light 54 incident on the interferometer 3; a beam splitter 52 that divides an interference wave 55 of the CW laser light 54 emitted from the interferometer 3; and a photodetector 53 that detects the interference wave 55 and converts the detected interference wave 55 into an electric signal.

In the case of the present embodiment, as the light source 50, QLD1061 manufactured by QD Laser, Inc., is used to emit CW laser light with a wavelength of 1064 nm.

The photodetector 53 is connected to the digitizer board of the PC 12 through a conductive wire 56, and the electric signal of the intensity of the interference wave 55 is transferred to the digitizer board. On the digitizer board, the electric signal is converted from analog to digital to be digital data. In the PC 12, for example, similarly to the intensity of the anti-Stokes light 15, the detection time and the intensity of the interference wave 55 are sequentially stored with the repetition period of the light pulse 13. In this manner, the interferogram of the interference wave 55 is produced. In the present embodiment, PDA10CF-EC, manufactured by Thorlabs, Inc., has been used as the photodetector 53, but another general photodetector is usable.

The CW laser light 54 that propagates in the first arm 21 and the CW laser light 54 that propagates in the second arm 22 interfere in the beam splitter 23 to strengthen or weaken each other in accordance with a difference in the light path length between the first arm 21 and the second arm 22 to become the interference wave 55, and hence the interferogram of the interference wave 55 is formed in such a shape as a sine wave of the intensity changing in a temporally periodic manner. In the region other than the vicinities of the initial position and the position B, the speed of the scanning mirror 26b is constant and the difference in the light path length changes in a temporally linear manner as described above, so that the frequency of the intensity is constant. In contrast, in the vicinities of the initial position and the position B, the speed of the scanning mirror 26b changes and the difference in the light path length changes in a temporally nonlinear manner as described above, so that the frequency of the intensity changes.

Therefore, by correcting the time axis such that the frequency of the intensity of the interferogram of the interference wave 55 becomes constant, the difference in the light path length can be corrected so as to change linearly. The correction made on the time axis of the interferogram of the interference wave 55 is also made on the time axis of the interferogram of the anti-Stokes light 15, to thereby correct the time axis such that the time of delay in the scanning light with respect to the reference light changes in a temporally linear manner also in the vicinities of the initial position and the position B.

Note that it is also possible to correct the interferogram of the anti-Stokes light 15 by using the interference wave 55 as a sampling clock to digitize the electric signal of the anti-Stokes light 15 on the digitizer board.

The delay in the scanning light with respect to the reference light in the interference wave 14 produced in the interferometer 3 periodically changes in accordance with the rotation angle of the scanning mirror 26b of the resonant scanner 26 from the initial position and becomes maximal in a half-period. Therefore, by taking out electronic data of an interferogram for the half-period of the change in the rotation angle of the scanning mirror 26b and performing a Fourier transform of the electronic data of the interferogram, the molecular vibration spectrum of the sample 7 can be acquired. In the present embodiment, a fast Fourier transform program stored in the storage of the PC 12 is executed by a processor (not shown in FIG. 1) of the PC 12 to perform a fast Fourier transform of the electronic data of the interferogram, and electronic data of a molecular vibration spectrum is acquired as stored into the storage of the PC 12. The PC 12 may be provided with display means for displaying the acquired molecular vibration spectrum.

In the present embodiment, the electric signal of the intensity of the anti-Stokes light 15 has been digitized using the digitizer board mounted in the PC 12, but a digitizer may be prepared separately from the PC 12 and the electric signal of the intensity of the anti-Stokes light 15 may be digitized by the digitizer.

In the present embodiment, the fast Fourier transform of the electronic data of the interferogram has been performed using the fast Fourier transform program stored in the storage of the PC 12, but hardware such as a circuit specialized for Fourier transform calculation may be prepared and a Fourier transform of the electronic data of the interferogram may be performed by the hardware.

In the above embodiment, the case has been described where the position closest to the beam splitter 23 is taken as the initial position of the scanning mirror 26b, but the present invention is not limited thereto, and the position farthest from the beam splitter 23 (the position B of the scanning mirror 26b, indicated by the solid line shown in FIG. 1) may be taken as the initial position of the scanning mirror 26b, and the constituent elements of the first arm 21 and the second arm 22 may be disposed such that the light path length of the reference light of the first arm 21 is the same as the light path length of the scanning light of the second arm 22 at the time when the scanning mirror 26b is at the initial position.

In this case, when the scanning mirror 26b is displaced from the initial position, the light path length of the scanning light becomes shorter, and the scanning light comes to reach the beam splitter 23 prior to the reference light. Hence the interferometer 3 produces the interference wave 14 in which the scanning light is advanced with respect to the reference light in accordance with the rotation angle of the scanning mirror 26b from the initial position.

In the above embodiment, the case has been described where the interferogram is produced using the anti-Stokes light 15 as scattered light emitted from the sample 7 to acquire a molecular vibration spectrum, but the present invention is not limited thereto, and an interferogram may be produced using the Stokes light as scattered light emitted from the sample 7 and a Fourier transform of the interferogram may be performed to acquire a molecular vibration.

In this case, the short pass filter 9 with its cutoff wavelength set to 850 nm is disposed in the position where the long pass filter 5 has been disposed shown in FIG. 1, and the long pass filter 5 with its cutoff wavelength set to 850 nm is disposed in the position where the short pass filter 9 has been disposed.

In this manner, the short pass filter 9 can prevent transmission of light at the bottom on the long wavelength side in the spectrum of the interference wave 14 to cut off light with a wavelength which is about the same as the wavelength of the Stokes light generated in the sample 7, and the long pass filter can remove the interference wave 14 transmitted through the sample 7 and most of the anti-Stokes light 15 emitted from the sample 7 and having a shorter wavelength than the interference wave 14. As a result, the Stokes light emitted from the sample 7 can be detected in the photodetector 10, an interferogram of the Stokes light can be produced, and a molecular vibration spectrum can be acquired from the Stokes light.

In the above embodiment, the case has been described where the light path length of the reference light of the first arm 21 is fixed and only the light path length of the scanning light of the second arm 22 is changed to delay the scanning light with respect to the reference light, but the present invention is not limited thereto, and the light path length of the reference light of the first arm 21 may also be changed to delay the scanning light with respect to the reference light.

In this case, for example, the first arm 21 is configured as is the second arm 22. That is, in place of the dispersion lens 24 and the first mirror 25, the first arm 21 includes a resonant scanner, a collector lens, and the mirror as those included in the second arm 22 in the same arrangement as in the second arm 22. In the first arm 21 as thus configured, this mirror serves as the first mirror.

When the scanning mirror (first scanning mirror) of the resonant scanner of the first arm 21 is at a position farthest from the beam splitter (a position corresponding to the position B of the scanning mirror 26b shown in FIG. 1), the position is taken as the initial position of the scanning mirror of the first arm 21. Further, the first arm 21 and the second arm 22 are adjusted such that the light path length of the reference light at the time of the scanning mirror of the first arm 21 being at the initial position is the same as the light path length of the scanning light at the time of the scanning mirror 26b (second scanning mirror) of the second arm 22 being at the initial position.

In this manner, when the rotating shaft of each scanning mirror rotates from the initial position, the reference light which propagates in the first arm 21 reaches the beam splitter 23 earlier than at the time when the scanning mirror is at the initial position, while the scanning light which propagates in the second arm 22 comes to reach the beam splitter 23 later than at the time when the scanning mirror is at the initial position, and the delay in the scanning light with respect to the reference light becomes larger than in the above embodiment. This delay becomes at most twice as large as that in the above embodiment. This enables measurement of a molecular vibration spectrum with higher resolution.

Note that the first arm 21 is not necessarily configured as is the second arm 22 and may be configured as is a second arm 22A, a second arm 22B, or a second arm 22C, described later. Also, in this case, in the first arm 21, when the scanning mirror rotates, it is preferable to adjust each constituent element such that the reference light reaches the beam splitter 23 earlier than at the time of the scanning mirror being at the initial position.

(2) Actions and Effects

In the above configuration, the Fourier transform-type spectroscopic device 1 of the present embodiment has been configured so as to include the interferometer 3 that includes the beam splitter 23 which splits the light pulse 13 of pulse laser light emitted from the light source 2 into reference light and scanning light, the first arm 21 which causes the reference light to be reflected on the first mirror 25 and incident again on the beam splitter 23, and the second arm 22 which causes the scanning light to be reflected on the second mirror 28 and incident again on the beam splitter 23, the interferometer 3 combining the reference light and the scanning light incident again on the beam splitter 23, to produce the interference wave 14.

Further, the Fourier transform-type spectroscopic device 1 of the present embodiment has been configured so as to include the photodetector 10 that detects intensity of the anti-Stokes light 15 (light to be detected), emitted from the inspection object 7 irradiated with the interference wave 14, and the optical spectrum production unit (PC 12) that produces an interferogram based on intensity of a plurality of beams of the anti-Stokes light 15 obtained by repeatedly irradiating the sample 7 with the interference wave 14 while changing the time of delay in the scanning light with respect to the reference light, and performs a Fourier transform of the interferogram.

Moreover, the Fourier transform-type spectroscopic device 1 of the present embodiment has been configured such that the second arm 22 includes the scanning mirror 26b of the resonant scanner 26 disposed on a light path of the scanning light between the beam splitter 23 and the second mirror 28, and delays the scanning light with respect to the reference light in accordance with the rotation angle of the scanning mirror 26b from the initial position.

Therefore, the Fourier transform-type spectroscopic device 1 of the present embodiment rotates the scanning mirror 26b by rotation of the rotating shaft 26a to change the light path length of the scanning light and delays the scanning light with respect to the reference light in accordance with the rotation angle of the scanning mirror 26b from an initial position and is thus capable of moving the scanning mirror 26b at a high speed by rotation of the rotating shaft 26a as compared with the case where the position of the movable mirror is moved to delay the scanning light with respect to the reference light as in the conventional Fourier transform-type spectroscopic device, thereby improving an acquisition speed of a molecular vibration spectrum.

Further, the Fourier transform-type spectroscopic device 1 of the present embodiment delays the scanning light with respect to the reference light by displacement of the scanning mirror 26b due to resonant vibration, and is thus capable of changing the light path length of the scanning light at a high speed as compared with the conventional Fourier transform-type spectroscopic device, thereby improving the acquisition speed of the molecular vibration spectrum. In addition, the Fourier transform-type spectroscopic device 1 repeatedly produces an interferogram by using periodic motion due to resonant vibration of the scanning mirror 26b, and is thus capable of reducing the time taken for acceleration and stopping as compared with the conventional Fourier transform-type spectroscopic device which needs to repeat acceleration and stopping of the movable mirror, and further improving the acquisition speed of the molecular vibration spectrum especially in the case of successively acquiring the molecular vibration spectrum of the sample 7.

Moreover, the Fourier transform-type spectroscopic device 1 of the present embodiment is capable of increasing the difference in the light path length between the reference light and the scanning light by incidence of the scanning light split in the beam splitter 23 on the vicinity of the outer edge of the scanning mirror 26b, thereby improving spectrum resolution.

(3) Modifications (3-1) Fourier Transform-Type Spectroscopic Device of First Modification In the following, a Fourier transform-type spectroscopic device of a first modification will be described. The Fourier transform-type spectroscopic device of the first modification is different from the Fourier transform-type spectroscopic device 1 of the above embodiment in the configuration of the interferometer, but the other configurations are similar, so the configuration of the interferometer will be described mainly.

Figure 2:
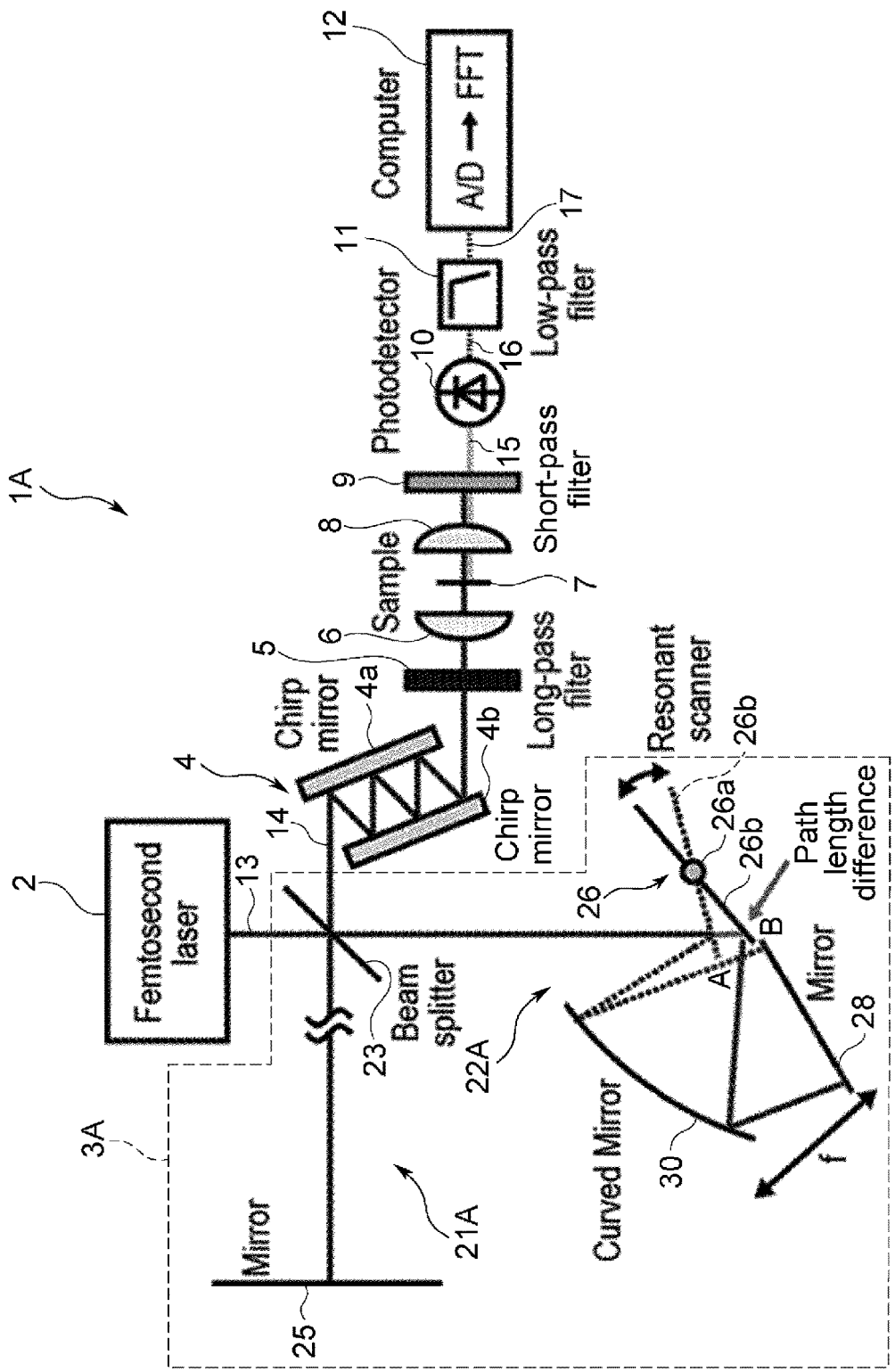
FIG. 2 is a schematic diagram showing an entire configuration of a Fourier transform-type spectroscopic device according to a modification of the present invention.

As shown in FIG. 2 where a configuration being the same as that of the Fourier transform-type spectroscopic device 1 of the embodiment shown in FIG. 1 is provided with the same numeral, an interferometer 3A of a Fourier transform-type spectroscopic device 1A is made up of the beam splitter 23, a first arm 21A including the first mirror 25, and a second arm 22A including the resonant scanner 26 similar to that in the Fourier transform-type spectroscopic device 1, a curved mirror 30, and the second mirror 28.

The first mirror 25 is a plane mirror and is disposed such that the mirror surface is vertical to the light path of the reference light split from the light pulse 13 by the beam splitter 23. Hence in the first arm 21A, the reference light is vertically incident on the first mirror 25, and the reference light reflected on the first mirror passes along the same path in the reverse direction and is incident again on the beam splitter 23.

The second arm 22A is configured such that the scanning light split in the beam splitter 23 is reflected on the scanning mirror 26b of the resonant scanner 26, which is then reflected on the curved mirror 30 and incident on the second mirror 28.

In the second arm 22A, the resonant scanner 26 is disposed similarly to the above embodiment, and the scanning mirror 26b performs periodic motion on the light path of the scanning light between an initial position and a position farthest from the beam splitter 23 (a position B of the scanning mirror 26b indicated by a solid line shown in FIG. 2), with a position that is closest to the beam splitter 23 (a position A of the scanning mirror 26b indicated by a broken line shown in FIG. 2) taken as the initial position. Hence in the second arm 22A, the distance between the beam splitter 23 and the scanning mirror 26b changes in accordance with the rotation angle of the scanning mirror 26b from the initial position, and as a result, the light path of the scanning light changes.

The scanning mirror 26b, the curved mirror 30, and the second mirror 28 are disposed such that the second mirror 28 is disposed adjacent to the scanning mirror 26b and that the curved mirror 30 is disposed so as to face the scanning mirror 26b and the second mirror 28, and are disposed such that an interval between the scanning mirror 26b and the curved mirror 30 and an interval between the curved mirror 30 and the second mirror 28 are the same as a focal distance f of the curved mirror 30. The curved mirror 30 reflects the incident scanning light and makes the scanning light vertically incident on the mirror surface of the second mirror 28 which is a plane mirror.

The sizes of the curved mirror 30 and the second mirror 28 are selected and the positions thereof are adjusted such that the scanning light reflected on the scanning mirror 26b is reflected on the curved mirror 30 and vertically incident on the second mirror 28 irrespective of the rotation angle of the scanning mirror 26b.

With the scanning light being vertically incident on the second mirror 28 as thus described, in the second arm 22A, when the scanning light is reflected on the second mirror 28, the scanning light passes along the same path in the reverse direction and is incident again on the beam splitter 23.

The reference light reflected on the first mirror 25 and the scanning light reflected on the second mirror 28 are incident on the beam splitter 23 to become the interference wave 14 as in the above embodiment. In the interferometer 3A, similarly to the above embodiment, the placement of the constituent elements of the first arm 21 and the second arm 22 is adjusted such that the light path length of the reference light of the first arm 21A is the same as the light path length of the scanning light of the second arm 22A at the time when the scanning mirror 26b is at the initial position.

Therefore, similarly to the above embodiment, in the interferometer 3A, when the scanning mirror 26b of the resonant scanner 26 is at the initial position (position A), the reference light which propagates in the first arm 21 and the scanning light which propagates in the second arm 22A simultaneously reach the beam splitter 23 and are superimposed to produce the interference wave 14, whereafter the scanning light is delayed with respect to the reference light in accordance with the rotation angle of the scanning mirror 26b (in accordance with the difference in the light path length between the reference light and the scanning light), and the scanning light in the state of being delayed with respect to the reference light is superimposed with the reference light, to produce the interference wave 14 which is a collinear light pulse.

In this manner, similarly to the interferometer 3 of the above embodiment, the interferometer 3A produces the interference wave 14 in which the scanning light is delayed with respect to the reference light in accordance with the rotation angle of the scanning mirror 26b from the initial position.

In the case of the present modification, the scanning light is made incident on the second mirror 28 by using the curved mirror 30 without using the collector lens 27, and hence the second arm 22A includes no element that causes occurrence of group velocity dispersion on the path of the scanning light. This eliminates the need for the first arm 21A to compensate the group velocity dispersion of the reference light, and it is thus possible to obtain a molecular vibration spectrum with high sensitivity without placement of the dispersion lens 24. This enables simple configuration of the interferometer 3A.

Although not shown in FIG. 2, the first modification has a configuration for correcting the time axis of the interferogram of the anti-Stokes light 15, which is similar to the above embodiment, and corrects the time axis of the interferogram of the anti-Stokes light 15 by a similar method to that in the above embodiment.

(3-2) Fourier Transform-Type Spectroscopic Device of Second Modification

In the following, a Fourier transform-type spectroscopic device of a second modification will be described. The Fourier transform-type spectroscopic device of the second modification is different from the Fourier transform-type spectroscopic device 1 of the above embodiment in the configuration of the interferometer, but the other configurations are similar, so the configuration of the interferometer will be described mainly.

Figure 3:
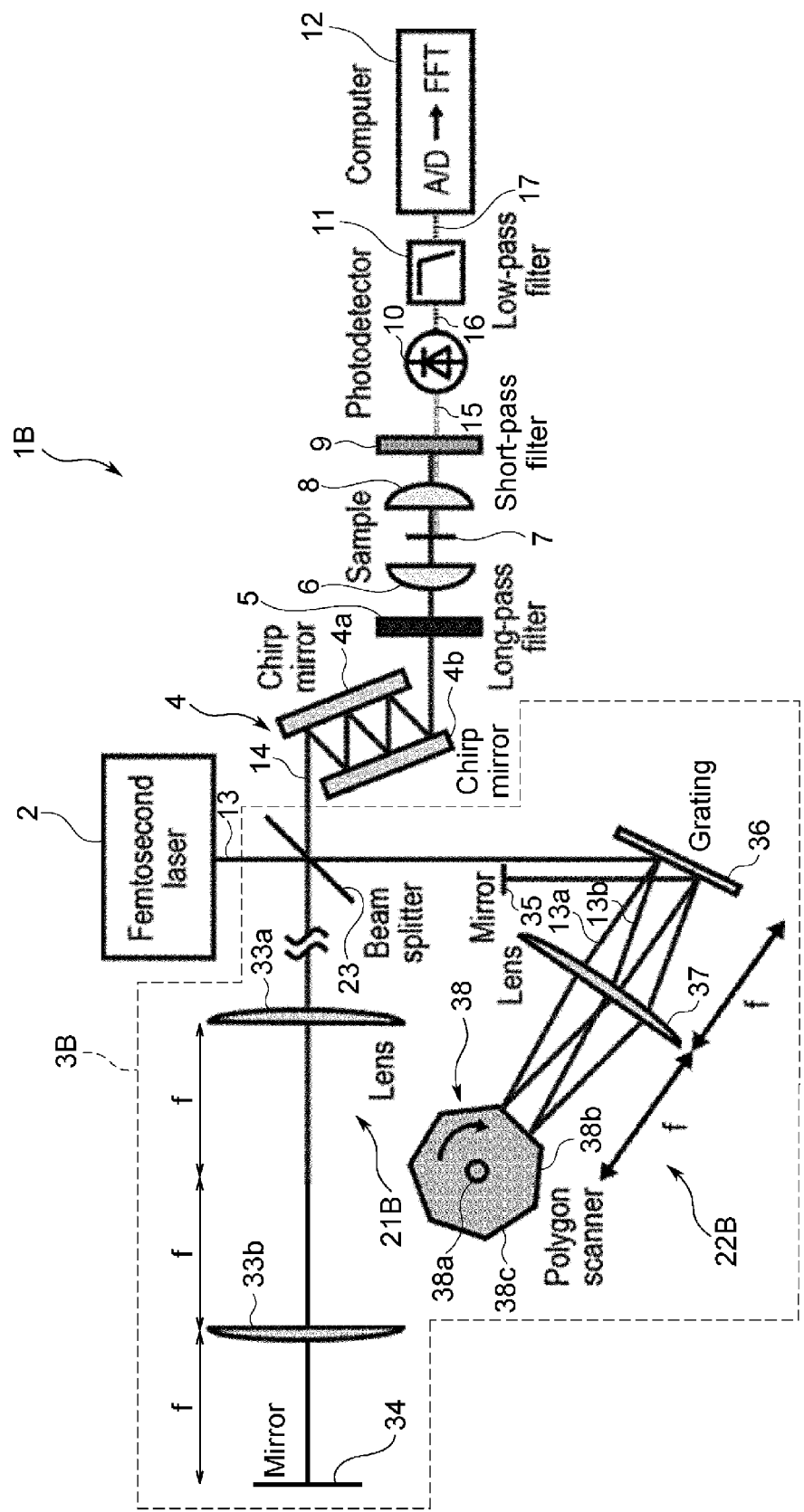
FIG. 3 is a schematic diagram showing an entire configuration of a Fourier transform-type spectroscopic device according to a modification of the present invention.

As shown in FIG. 3 where a configuration being the same as that of the Fourier transform-type spectroscopic device 1 of the embodiment shown in FIG. 1 is provided with the same numeral, an interferometer 3B of a Fourier transform-type spectroscopic device 1B is made up of the beam splitter 23, a first arm 21B including dispersion lenses 33a, 33b and a first mirror 34, and a second arm 22B including a diffractive optical element 36, a collector lens 37, a polygon scanner 38, and a second mirror 35.

The first arm 21B is configured such that the reference light is transmitted through the dispersion lenses 33a, 33b and incident on the first mirror 34. The dispersion lenses 33a, 33b are lenses similar to the collector lens 37 of the second arm 22B, described later, and disposed on the light path of the reference light. In the second arm 22B, the scanning light is transmitted through the collector lens 37 twice before reaching the second mirror 35 from the beam splitter 23, and hence the first arm 21B includes two dispersion lenses 33a, 33b. The dispersion lenses 33a, 33b cause occurrence of group velocity dispersion in the reference light, which is similar to the group velocity dispersion having occurred in the scanning light by the scanning light being transmitted through the collector lens 37 twice, so that the pulse shapes of the reference light and the scanning light can be made uniform.

Such dispersion lenses 33a, 33b are disposed at an interval twice as large as a focal distance f of the dispersion lens 33a, namely, a distance 2f. Further, in the present modification, the first mirror 34 is disposed at a distance from the dispersion lens 33b which is the same as a focal distance f of the dispersion lens 33b, and the dispersion lens 33a, the dispersion lens 33b, and the first mirror 34 constitute a so-called 4f optical system. Note that the dispersion lens 33a and the dispersion lens 33b may only be disposed at an interval of 2f, and there is no need that the dispersion lens 33a, the dispersion lens 33b, and the first mirror 34 constitute the 4f optical system. Although the first arm 21B preferably includes the two dispersion lenses 33a, 33b, the first arm 21B may not include the dispersion lens or may include only one dispersion lens.

The first mirror 34 is a plane mirror and is disposed vertically to the light beam of the reference light emitted from the beam splitter 23, and the reference light is vertically incident on the mirror surface. Therefore, in the first arm 21B, when the reference light is reflected on the first mirror 34, the reflected light passes along the same path in the reverse direction and is incident again on the beam splitter 23.

The second arm 22B is configured such that the scanning light diffracted in the diffractive optical element 36 is collected on a scanning mirror 38b of the polygon scanner 38 by the collector lens 37, and the scanning light reflected on the scanning mirror 38b is incident again on the collector lens 37 and collected on the diffractive optical element 36 by the collector lens 37. Further, the second arm 22B is configured such that the scanning light collected on the diffractive optical element 36 is combined, which is then incident on the second mirror 35.

The diffractive optical element 36 is, for example, a platy diffraction grating obtained by forming about 600 grooves per 1 mm on the surface of a metal plate, and the scanning light is diffracted and split into light beams with respective wavelength components. A plurality of wavelength components with different wavelengths contained in the scanning light which is a light pulse are divided for each wavelength, and the scanning light is thus divided into light beams with the respective wavelength components and becomes light in which the light beams with the respective wavelength components are distributed in one dimension. For convenience of description, FIG. 3 represents the diffracted scanning light by using two light beams which are a scanning light beam 13a corresponding to a light beam with a wavelength component having the shortest wavelength in the scanning light and a scanning light beam 13b corresponding to a light beam with a wavelength component having the longest wavelength in the scanning light, but in practice, the divided light beams with the respective wavelength components are continuously arranged between the scanning light beam 13a and the scanning light beam 13b. In the following, the scanning light beams 13a, 13b will be described as typical scanning light beams diffracted in the diffractive optical element 36. Description on the scanning light beam 13a and the scanning light beam 13b also applies to the light beams with the other frequency components. As the diffractive optical element 36, a diffraction grating with the number of grooves per 1 mm being about 300 to 600 or another form of the diffraction grating is also usable.

The diffractive optical element 36, the collector lens 37, and the scanning mirror 38b are disposed such that an interval between the diffractive optical element 36 and the collector lens 37 and an interval between the collector lens 37 and the scanning mirror 38b are the same as a focal distance f of the collector lens 37, thereby constituting a so-called 4f optical system. The collector lens 37 refracts the incident scanning light beams 13a, 13b, collects the scanning light beams 13a, 13b, divided in the diffractive optical element 36, on the scanning mirror 38b, and collects the scanning light beams 13a, 13b, reflected on the scanning mirror 38b, on the diffractive optical element 36.

The polygon scanner 38 includes: a rotator 38c in the shape of a polygonal pillar provided with a rotating shaft 38a at the center; a plurality of scanning mirrors 38b disposed on the respective side surfaces of the rotator 38c; a motor (not shown in FIG. 3) that is connected to the rotating shaft 38a and rotates the rotating shaft 38a to rotate the rotator 38c; and a rotation control unit (not shown in FIG. 3) that controls the motor to control rotation of the rotator 38c, and the polygon scanner 38 performs periodic motion in which the rotator 38c rotates in a constant direction around the rotating shaft 38a by rotation of the rotator 38c. The scanning mirror 38b also performs periodic motion by rotation of the polygon scanner 38.

In the case of the present modification, a heptahedral polygon laser scanner, manufactured by NIDEC COPAL CORPORATION, is used as the polygon scanner 38, and the scanning mirror 38b is provided on each of seven side surfaces of the rotator 38c in the shape of a heptahedral pillar with an inscribed circle diameter of 40 mm. The polygon scanner 38 performs periodic motion clockwise at a frequency of 167 Hz. That is, the polygon scanner 38 rotates clockwise with a period of 6 ms. As the polygon scanner 38, for example, a commercially available general polygon scanner, such as RTA series manufactured by Lincoln Laser Company, is usable.

In the interferometer 3B, the rotator 38c of the polygon scanner 38 rotates clockwise in a direction of an arrow in FIG. 3, and when the scanning mirror 38b becomes parallel to the focal plane (Fourier plane) of the scanning light diffracted in the diffractive optical element 36, the distance between the diffractive optical element 36 and a position of the scanning mirror 38b to which the scanning light beam 13a is applied becomes the same as the distance between the diffractive optical element 36 and a position of the scanning mirror 38b to which the scanning light beam 13b is applied. As a result, the light path length of the scanning light beam 13a and the light path length of the scanning light beam 13b become the same. At this time, the light path lengths of the light beams with the other wavelength components, split in the diffractive optical element 36, are the same.

Thereafter, the scanning mirror 38b further rotates by rotation of the rotating shaft 38a, its inclination changes, and one end of the scanning mirror 38b in the rotating direction becomes farther from the diffractive optical element 36 while the other end becomes closer to the diffractive optical element 36 side. As a result, the position of the scanning mirror 38b to which the scanning light beam 13b is applied moves to the back side with respect to the diffractive optical element 36, and the position to which the scanning light beam 13a is applied moves to the front side with respect to the diffractive optical element 36. Hence the distance between the diffractive optical element 36 and the position of the scanning mirror 38b to which the scanning light beam 13a is applied becomes different from the distance between the diffractive optical element 36 and the position of the scanning mirror 38b to which the scanning light beam 13b is applied. Therefore, the light path length of the scanning light beam 13a between the diffractive optical element 36 and the scanning mirror 38b becomes different from the light path length of the scanning light beam 13b between the diffractive optical element 36 and the scanning mirror 38b. Then, the light beams with the respective wavelength components between the scanning light beam 13a and the scanning light beam 13b become different in the light path length in accordance with the inclination of the scanning mirror 38b. As thus described, the scanning light beams with the respective wavelength components have different light path lengths.

When the rotating shaft 38a further rotates, the scanning mirror 38b is further inclined and one end thereof in the rotating direction becomes still farther while the other end becomes still closer, so that a difference in the light path length between the scanning light beam 13a and the scanning light beam 13b becomes larger, and the difference in the light path length among the light beams with the respective wavelength components becomes larger.

When the position of the scanning mirror 38b at the time of the scanning mirror 38b becoming parallel to the focal plane of the scanning light diffracted in the diffractive optical element 36 is taken as the initial position, the scanning mirror 38b rotates from the initial position by periodic motion of the rotator 38c by rotation of the rotating shaft 38a, and the larger the angle of rotation of the scanning mirror 38b from the initial position by the periodic motion becomes, the larger the difference in the light path length between the scanning light beam 13a and the scanning light beam 13b becomes. Here, the rotation angle of the scanning mirror 38b is a rotation angle of the rotating shaft 38a at the time when the scanning mirror 38b rotates.

In the case of the present modification, the difference in the light path length between the scanning light beam 13a and the scanning light beam 13b increases due to the increase in the rotation angle of the scanning mirror 38b from the initial position until the scanning light beam 13a is applied to the boundary with the adjacent scanning mirror 38b.

Thereafter, when the rotating shaft 38a further rotates, the scanning light beam 13a is applied to the scanning mirror 38b adjacent to the scanning mirror 38b to which the scanning light beam 13b is currently applied, and the scanning light comes to be applied over two adjacent scanning mirrors 38b. When the rotating shaft 38a further rotates, the scanning light beam 13b also comes to be applied to the scanning mirror 38b, to which the scanning light beam 13a is currently applied, and the reference light comes to be applied to one scanning mirror 38b again. When the rotating shaft 38a further rotates, the focal plane of the scanning light becomes parallel to the scanning mirror 38b, and this scanning mirror 38b moves to the initial position.

With the polygon scanner 38 including the plurality of scanning mirrors 38b, the above process is repeated for each of the plurality of scanning mirrors 38b, and the increase and decrease of the difference in the light path length between the scanning light beam 13a and the scanning light beam 13b are repeated by rotation of the rotating shaft 38a. Note that the time from application of the scanning light over two adjacent scanning mirrors 38b to application of the scanning light to one scanning mirror 38b again, and to movement of the scanning mirror 38b to the initial position is a dead time when a molecular vibration spectrum cannot be acquired.

The scanning light beams 13a, 13b reflected on the scanning mirror 38b are collected on the collector lens 37 and incident on the diffractive optical element 36. The scanning light beams 13a, 13b are combined in the diffractive optical element 36 to become a light pulse, which is then emitted from the diffractive optical element 36. The scanning light emitted from the diffractive optical element 36 is incident on the second mirror 35 which is a plane mirror. The second mirror 35 is disposed such that the scanning light emitted from the diffractive optical element 36 is vertically incident on the mirror surface. With the scanning light being vertically incident on the second mirror 35 as thus described, the scanning light reflected on the second mirror 35 passes along the same path in the reverse direction and is incident again on the beam splitter 23.

The reference light reflected on the first mirror 34 and the scanning light reflected on the second mirror 35 are incident on again the beam splitter 23 and interfere with each other to become the interference wave 14. In the interferometer 3B, the placement of the constituent elements of the first arm 21B and the second arm 22B is adjusted such that the light path length of the reference light of the first arm 21B (the light path length of the reference light in reciprocation between the beam splitter 23 and the first mirror 34) is the same as the light path length of the scanning light of the second arm 22B (the light path length of the scanning light in reciprocation between the beam splitter 23 and the second mirror 35) at the time when the scanning mirror 38b of the polygon scanner 38 is at the initial position.

For this reason, when the scanning mirror 38b is at the initial position, the scanning light which propagates in the second arm 22B reaches the beam splitter 23 without a delay with respect to the reference light which propagates in the first arm 21B, and because the reference light and the scanning light are split from the same light pulse 13, the reference light and the scanning light are superimposed to strengthen each other and produce the interference wave 14.

In contrast, when the rotation angle of the scanning mirror 38b of the polygon scanner 38 from the initial position increases, a difference in the light path length is generated between the scanning light beam 13a and the scanning light beam 13b, and difference in the light path length becomes larger in accordance with the increase in the rotation angle. At this time, the distance between the diffractive optical element 36 and the position of the scanning mirror 38b to which the scanning light beam is applied is the longest when the above position is a position of the scanning mirror 38b to which the scanning light beam 13b (the light with the longest wavelength in the reference light) is applied, and the distance is the shortest when the above position is a position of the scanning mirror 38b to which the scanning light beam 13a (the light with the shortest wavelength in the reference light) is applied.

The scanning light beams with the respective wavelength components are arranged between the scanning light beam 13a and the scanning light beam 13b in ascending order of the wavelength, and the surface of the scanning mirror 38b is linearly irradiated with the scanning light beams, so that the wavelength of the scanning light beam that is applied to the scanning mirror 38b becomes longer from the position to which the scanning light beam 13a is applied toward the position to which the scanning light beam 13b is applied. For this reason, the distance between the diffractive optical element 36 and the position of the scanning mirror 38b to which the scanning light beam with each wavelength component is applied becomes longer as the wavelength of the scanning light beam with each wavelength component becomes longer, and changes linearly in proportion to the wavelength. Hence the light path length of each wavelength component also changes linearly in proportion to the wavelength.

When the scanning light beams with the respective wavelength components are combined in the diffractive optical element 36, a phase delay occurs in the light beam with each wavelength component in accordance with the difference in the light path length from the scanning light beam 13a having the shortest light path length. Because the light path length of the light beam with each wavelength component changes linearly in proportion to the wavelength, the phase delay also changes linearly in proportion to the wavelength.

As a result, when the scanning light is combined in the diffractive optical element 36, the phase states of the scanning light beams with the respective wavelength components change, to cause a change in the timing when the phases of the light beams with the respective wavelength components become uniform, and a group delay occurs. The phase state of light means a superimposing condition of the light beam with each wavelength component, namely, the degree of delay in the phase of each wavelength component. At this time, the delay in the phase of each wavelength component linearly changes, so that the pulse width of the scanning light does not increase and the group delay occurs. The difference in the light path length between the scanning light beam 13a and the scanning light beam 13b increases in proportion to the rotation angle of the scanning mirror 38b, and hence the group delay of the scanning light also increases in proportion to the rotation angle of the scanning mirror 38b.

In this manner, the second arm 22B delays the scanning light in accordance with the rotation angle of the scanning mirror 38b. Due to the delay occurring in the scanning light, the scanning light comes to reach the beam splitter 23 with a delay with respect to the reference light. At this time, the interference wave 14 becomes a collinear light pulse obtained by alignment of the reference light and the delayed scanning light on the same light axis and superimposition of the scanning light in the delayed state on the reference light.

The delay in the scanning light with respect to the reference light changes in accordance with the rotation angle of the scanning mirror 38b because the difference in the light path length among the scanning light beams with the respective wavelength components changes in accordance with the rotation angle of the scanning mirror 38b and the time of delay in the light beam with each wavelength component changes. In the case of the present modification, when the scanning light beam 13a is applied to the boundary of the adjacent scanning mirror 38b, the delay in the scanning light with respect to the reference light becomes maximal, and the rotation angle of the scanning mirror 38b from the initial position is taken as the maximum value of the rotation angle.

The rotator 38c rotates at a constant speed and the rotation angle of the scanning mirror 38b also changes at a constant speed, so that in a period of time until the rotation angle from the initial position becomes the maximum value, the delay in the scanning light with respect to the reference light changes in a temporally linear manner. Therefore, the intensity of the anti-Stokes light 15, detected in the period of time until the rotation angle from the initial position becomes the maximum value, is used for producing the interferogram, thereby eliminating the need to correct the time axis as in the above embodiment.

In this manner, the interferometer 3B makes a difference in the light path length among the respective wavelength components of the scanning light beams in accordance with the rotation angles of the scanning mirror 38b from the initial position and varies the phase state of each of the wavelength components in the scanning light, to produce the interference wave 14 in which the scanning light is delayed with respect to the reference light.

In the Fourier transform-type spectroscopic device 1B, the interferogram is produced in the period of time until the rotation angle of the scanning mirror 38b from the initial position becomes the maximum value, and a Fourier transform of the interferogram is performed, so that the molecular vibration spectrum of the sample 7 can be acquired.

As above, the Fourier transform-type spectroscopic device 1B of the second modification rotates the scanning mirror 38b by rotation of the rotating shaft 38a to change the light path length of the scanning light beam with each wavelength component and delay the scanning light with respect to the reference light in accordance with the rotation angle of the scanning mirror 38b from the initial position, and is thus capable of moving the scanning mirror 38b at a high speed by rotation of the rotating shaft 38a as compared with the case where the position of the movable mirror is moved to delay the scanning light with respect to the reference light as in the conventional Fourier transform-type spectroscopic device, thereby improving the acquisition speed of the molecular vibration spectrum.

Further, the Fourier transform-type spectroscopic device 1B of the second modification can cause the rotator 38c to keep rotating in a constant direction to successively acquire a molecular vibration spectrum for each scanning mirror 38b of the rotator 38c, so that it is possible to eliminate the time taken for acceleration and stopping of the movable mirror as compared with the conventional Fourier transform-type spectroscopic device which needs to repeat acceleration and stopping of the movable mirror, and further improve the acquisition speed of the molecular vibration spectrum especially in the case of successively acquiring the molecular vibration spectrum of the sample 7. Moreover, the Fourier transform-type spectroscopic device 1B of the second modification can acquire molecular vibration spectra in number corresponding to the number of scanning mirrors 38b provided in the rotator 38c while the rotator 38c turns around once, thereby further improving the acquisition speed of the molecular vibration spectrum in the case of successively acquiring the molecular vibration spectrum.

In addition, as in the above embodiment, the scanning light may be advanced with respect to the reference light. For example, the rotator 38c is made to rotate in a counterclockwise direction, and a position to which the scanning light beam 13a is applied at the time of application of the scanning light beam 13a to the boundary of the adjacent scanning mirror 38b is taken as the initial position of the scanning mirror 38b. Then, when the scanning mirror 38b is at the initial position, the positions of the constituent elements of the first arm 21B are adjusted to change the light path length of the reference light such that there is no delay in the scanning light with respect to the reference light. In this manner, the scanning light can be advanced with respect to the reference light.

Note that the rotational frequency of the rotator 38c, the number of planes of the scanning mirror 38b, and the inscribed circle diameter of the rotator 38c can be selected as appropriate in accordance with parameters (repetition frequency, pulse width, etc.) of the light pulse 13 to be used and a target measuring rate.

For example, when the light source 2 that emits the light pulse 13 with a pulse width of 17 fs at a repetition frequency of 75 MHz is used as in the above embodiment, the polygon scanner 38 including the rotator 38c in the shape of a 54-sided pillar with an inscribed circle diameter of 60 mm is used and the rotator 38c is rotated at a frequency of 916.7 Hz, to generate a delay in the scanning light with respect to the reference light, which corresponds to about 1 mm in terms of the difference in the light path length, thus enabling measurement at a measuring rate of about 50 kHz.

When the number of planes increases, the measuring speed is improved, whereas the spectrum resolution decreases. For this reason, the rotator 38c desirably has a pillar shape with the number of apexes equal to or smaller than 54. If the number of apexes further increases and the number of planes of the scanning mirror 38b increases, the spectrum resolution further decreases.

(3-3) Fourier Transform-Type Spectroscopic Device of Third Modification

The Fourier transform-type spectroscopic device of the third modification is different from the Fourier transform-type spectroscopic device 1B in that the polygon scanner of the second arm 22B of the Fourier transform-type spectroscopic device 1B of the second modification is changed to a resonant scanner. The other configurations are the same and the description thereof is thus omitted.

Figure 4:
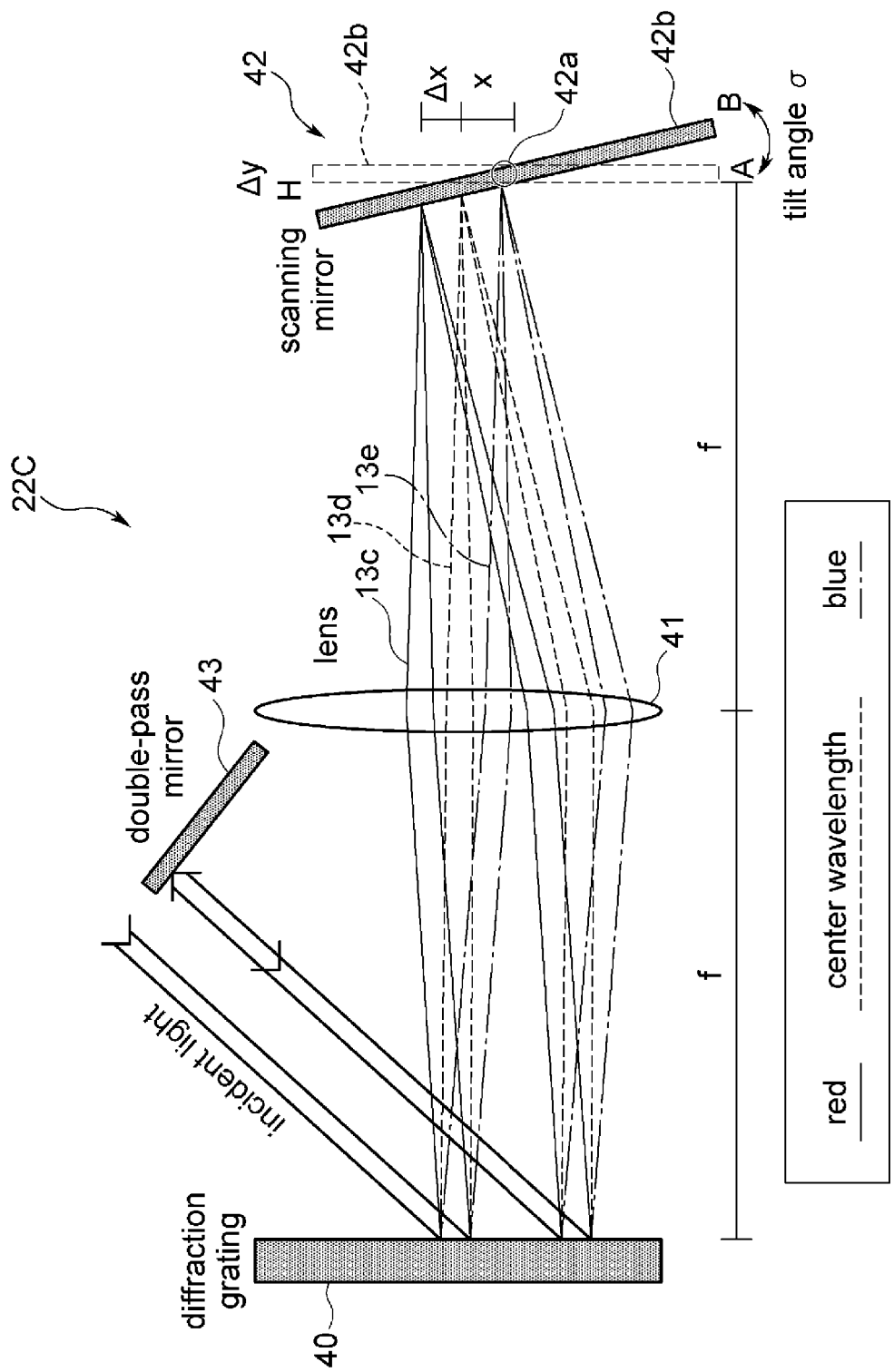
FIG. 4 is a schematic diagram showing a second arm of a Fourier transform-type spectroscopic device according to a modification of the present invention.

As shown in FIG. 4, a second arm 22C is configured such that scanning light diffracted and split in a diffractive optical element 40 is collected on a scanning mirror 42b of a resonant scanner 42 by a collector lens 41 and reflected on the scanning mirror 42b, which is then incident again on the collector lens 41 and corrected on the diffractive optical element 40 by the collector lens 41. Further, the second arm 22C is configured such that the scanning light collected on the diffractive optical element 40 is combined and the combined light is incident on a second mirror 43.

The configuration of the diffractive optical element 40 is similar to that of the second modification. For convenience of description, FIG. 4 represents the split scanning light by using three light beams which are a scanning light beam 13c corresponding to a light beam with a wavelength component having the longest wavelength in the scanning light, a scanning light beam 13d corresponding to a light beam with a wavelength component having an intermediate wavelength in the scanning light, and a scanning light beam 13e corresponding to a light beam with a wavelength component having the shortest wavelength in the scanning light, but the divided light beams with the respective wavelength components are continuously arranged between the scanning light beam 13c and the scanning light beam 13d and between the scanning light beam 13d and the scanning light beam 13e. In the following, the scanning light beams 13c, 13d, 13e will be described as typical scanning light beams split in the diffractive optical element 40. Description on the scanning light beams 13c, 13d, 13e also applies to the light beams with the other frequency components.

The collector lens 41 is disposed so as to be parallel to the diffractive optical element 40 at a distance from the diffractive optical element 40 which is the same as a focal distance of the collector lens 41. The collector lens 41 refracts the incident scanning light beams 13c, 13d, 13e, collects the scanning light beams 13c, 13d, 13e on the scanning mirror 42b, and collects the scanning light beams 13c, 13d, 13e, reflected on the scanning mirror 42b, on the diffractive optical element 40.

The resonant scanner 42 has a similar configuration to that of the resonant scanner 26 of the above embodiment, and the scanning mirror 42b is disposed in a state parallel to the collector lens 41 at a distance from the collector lens 41 which is the same as a focal distance f of the collector lens 41. In this manner, the diffractive optical element 40, the collector lens 41, and the scanning mirror 42b constitute a so-called 4f optical system.

The scanning mirror 42b of the resonant scanner 42 performs resonant vibration by rotation of a rotating shaft 42a to perform periodic motion between an initial position which is a position farthest from the collector lens (a position A indicated by a broken line shown in FIG. 4) and a position closest to the collector lens 41 (a position B indicated by a solid line shown in FIG. 4). The mirror surface of the scanning mirror 42b at the initial position is made parallel to the focal plane (Fourier plane) of the scanning light collected on the collector lens 41, at the initial position.

When the scanning mirror 42b is at the initial position, the light path lengths of the scanning light beams 13c, 13d, 13e are the same, and the light path lengths of the scanning light beams with the respective wavelength components are the same. Hence, when reaching the diffractive optical element 40, the scanning light beams with the respective wavelength components have phases that are uniform, and when the light beams with the respective wavelength components are combined in the diffractive optical element 40, no delay occurs in the scanning light.

In contrast, when the scanning mirror 42b rotates due to resonant vibration generated by rotation of the rotating shaft 42a and the rotation angle of the scanning mirror 42b from the initial position changes, the distance between the scanning mirror 42b and the diffractive optical element 40 changes. At this time, a displacement amount of the scanning mirror 42b increases toward the outer edge of the scanning mirror 42b, and hence the distance between the scanning mirror 42b and the diffractive optical element 40 becomes shorter as the position to which the scanning light beam with each wavelength component is applied gets closer to the outer edge of the scanning mirror 42b. Thus, among the light beams with the respective wavelength components, the scanning light beam 13c applied to the position closest to the outer edge of the scanning mirror 42b has the shortest light path length, and the scanning light beam 13e applied to the position farthest from the outer edge of the scanning mirror 42b has the longest light path length. Similarly to the above second modification, the light path length changes linearly in proportion to the wavelength of the light beam with each wavelength component. The time of delay in the light beam with each wavelength component changes linearly in proportion to the wavelength of the light beam with each wavelength component.

As a result, when the scanning light is combined in the diffractive optical element 36, the phase states of the scanning light beams with the respective wavelength components change, to cause a change in the timing when the phases of the light beams with the respective wavelength components become uniform, and group delay occurs in the scanning light. In this manner, similarly to the second arm 22B, the second arm 22C causes occurrence of the group delay in the scanning light in accordance with the rotation angle of the scanning mirror 42b.

In the second arm 22C of the third modification, the resonant scanner 42 is provided in place of the polygon scanner 38 of the second arm 22B of the second modification, so that it is possible to simplify the configuration of the second arm 22C and reduce the size of the Fourier transform-type spectroscopic device.

In the present modification, the use of the scanning mirror 42b of the resonant scanner 42 makes it possible to produce the interference wave 14 at the same interval as the repetition frequency of the light pulse 13, and possible to eliminate the state in which the interference wave 14 is not produced despite production of the light pulse 13 and to eliminate the dead time when the molecular vibration spectrum cannot be acquired.

In the present modification, the molecular vibration spectrum has been acquired by using only the interferogram of the anti-Stokes light 15 in the time region where the delay in the scanning light with respect to the reference light changes linearly, but as in the above embodiment, the time axis of the interferogram of the anti-Stokes light 15 may be corrected.

(3-4) Fourier Transform-Type Spectroscopic Device of Fourth Modification

In each of the above embodiment and first to third modifications, the description has been given of the Fourier transform-type spectroscopic device which obtains the molecular vibration spectrum from the anti-Stokes light 15 generated in coherent anti-Stokes Raman scattering (CARS), but the present invention is not limited thereto, and a Fourier transform-type spectroscopic device of the present invention can be modified so as to acquire a molecular vibration spectrum based on light absorption characteristics of the sample.

Figure 5:
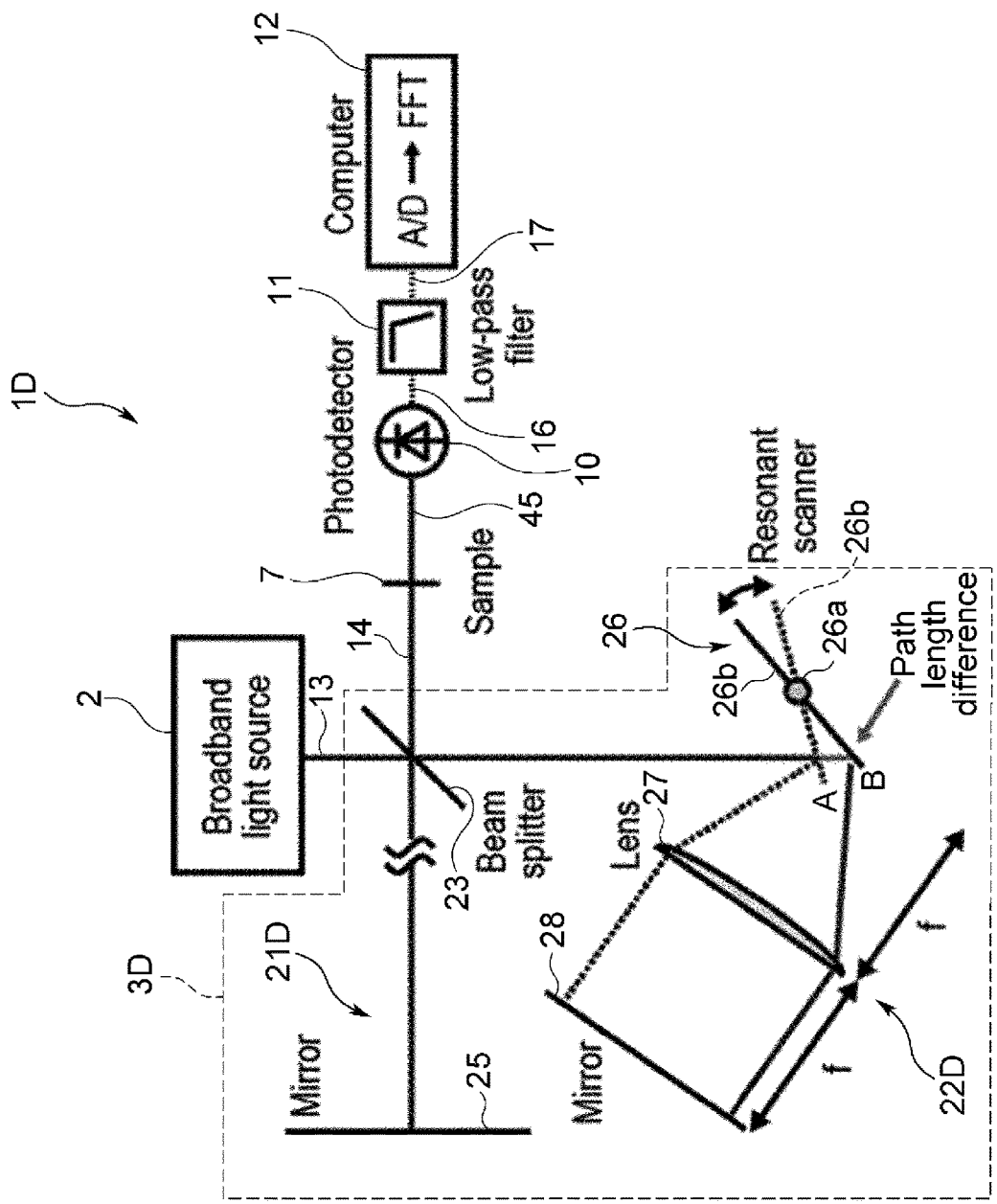
FIG. 5 is a schematic diagram showing an entire configuration of a Fourier transform-type spectroscopic device according to a modification of the present invention.

The Fourier transform-type spectroscopic device of the fourth embodiment is obtained by modifying the Fourier transform-type spectroscopic device 1 of the above embodiment so as to acquire a molecular vibration spectrum based on light absorption characteristics of the sample 7. In this case, as shown in FIG. 5 where a configuration similar to that of the Fourier transform-type spectroscopic device 1 of the embodiment shown in FIG. 1 is provided with the same numeral, a Fourier transform-type spectroscopic device 1D includes the light source 2, an interferometer 3D, the photodetector 10, the low-pass filter 11, and the PC 12. The Fourier transform-type spectroscopic device 1D is a Fourier transform-type spectroscopic device that uses the interferometer 3 to produce an interferogram of transmitted light 45 as light to be detected, generated by transmission of the interference wave 14 through the sample 7, and performs a Fourier transform of the interferogram by using the PC 12 to obtain a molecular vibration spectrum.

In the Fourier transform-type spectroscopic device 1D, differently from the Fourier transform-type spectroscopic device 1, the long pass filter 5 and the short pass filter 9 have been removed so as to detect the transmitted light 45 emitted from the sample 7. Further, absorption of light in the sample 7 is not a nonlinear optical phenomenon such as coherent anti-Stokes Raman scattering, but is a linear optical phenomenon, and hence the Fourier transform-type spectroscopic device 1D may not be provided with the compensator 4, the first objective lens 6, the second objective lens 8, or the dispersion lens 24. Therefore, in the Fourier transform-type spectroscopic device 1D, a first arm 21D does not include a dispersion lens and does not include a compensator, a first objective lens, nor a second objective lens. The other configuration of the Fourier transform-type spectroscopic device 1D, such as a second arm 22D, is the same as that of the Fourier transform-type spectroscopic device 1, with the same function provided, and hence the description thereof is omitted.

The interferometer 3D has a similar function to that of the interferometer 3 and produces the interference wave 14 in which the scanning light is delayed with respect to the reference light in accordance with the rotation angle of the scanning mirror 26b from the initial position.

When the interference wave 14 is applied to the inspection object 7, in the process of transmission through the sample 7, among wavelength components contained in the reference light and the scanning light, the intensity of light with a wavelength component corresponding to molecular vibration contained in the sample 7 decreases and the light is emitted as the transmitted light 45 from the sample 7.

In the Fourier transform-type spectroscopic device 1D, each time the light pulse 13 is produced in the light source 2, the transmitted light 45 generated by transmission of the interference wave 14 through the sample is sequentially stored as electronic data, to thereby produce an interferogram having a value of the intensity of the transmitted light 45 at the same time interval as the repetition period of the light pulse 13. The delay in the scanning light with respect to the reference light in the interference wave 14 produced in the interferometer 3D periodically changes in accordance with the rotation angle of the scanning mirror 26 from the initial position of the resonant scanner 26 and becomes maximal in a half-period. Therefore, by taking out the interferogram for the half-period of the change in the rotation angle of the scanning mirror 26b and performing a Fourier transform of the interferogram, the molecular vibration spectrum of the sample 7 can be acquired.

The case has been described above where the Fourier transform-type spectroscopic device 1 of the embodiment is modified so as to acquire the molecular vibration spectrum based on the light absorption characteristics of the sample, but the present invention is not limited thereto, and the Fourier transform-type spectroscopic devices 1A, 1B of the first and second modifications and a Fourier transform-type spectroscopic device obtained by applying the second arm 22C of the third modification to the Fourier transform-type spectroscopic device 1B can also be modified to acquire a molecular vibration spectrum. Also, in this case, similarly to the Fourier transform-type spectroscopic device 1D of the fourth modification, it is configured such that the interferogram of transmitted light 45 as light to be detected, generated by transmission of the interference wave 14 through the sample 7, is produced.

Further, the broadband pulse laser has been used as the light source 2 in the present modification, but an incoherent light source such as a high-luminance ceramic light source or a halogen lamp is also usable as the light source 2. In this case, the reference light and the scanning light are not light pulses but continuous waves.

In the present modification, the molecular vibration spectrum has been acquired by using only the interferogram of the transmitted light 45 in the time region where the delay in the scanning light with respect to the reference light changes linearly, but as in the above embodiment where the time axis of the interferogram is corrected, the time axis of the interferogram of transmitted light 45 may be corrected.

In the present modification, the case has been described where the interferogram is produced using the transmitted light 45 emitted from the sample 7 as the light to be detected, to acquire the molecular vibration spectrum based on the light absorption characteristics, but the present invention is not limited thereto, and an interferogram may be produced using reflected light that is generated by reflection of the interference wave 14 on the sample 7 as light to be detected, and a Fourier transform of the interferogram may be performed to acquire a molecular vibration spectrum based on the light absorption characteristics.

In this case, reflected light from the sample 7 is acquired using a technique used in FT-IR in which the light absorption characteristics are acquired by using reflected light from a sample, such as regular reflection, attenuated total reflection (also referred to as ATR), or diffuse reflection.

(4) Verification Test

Figure 6:
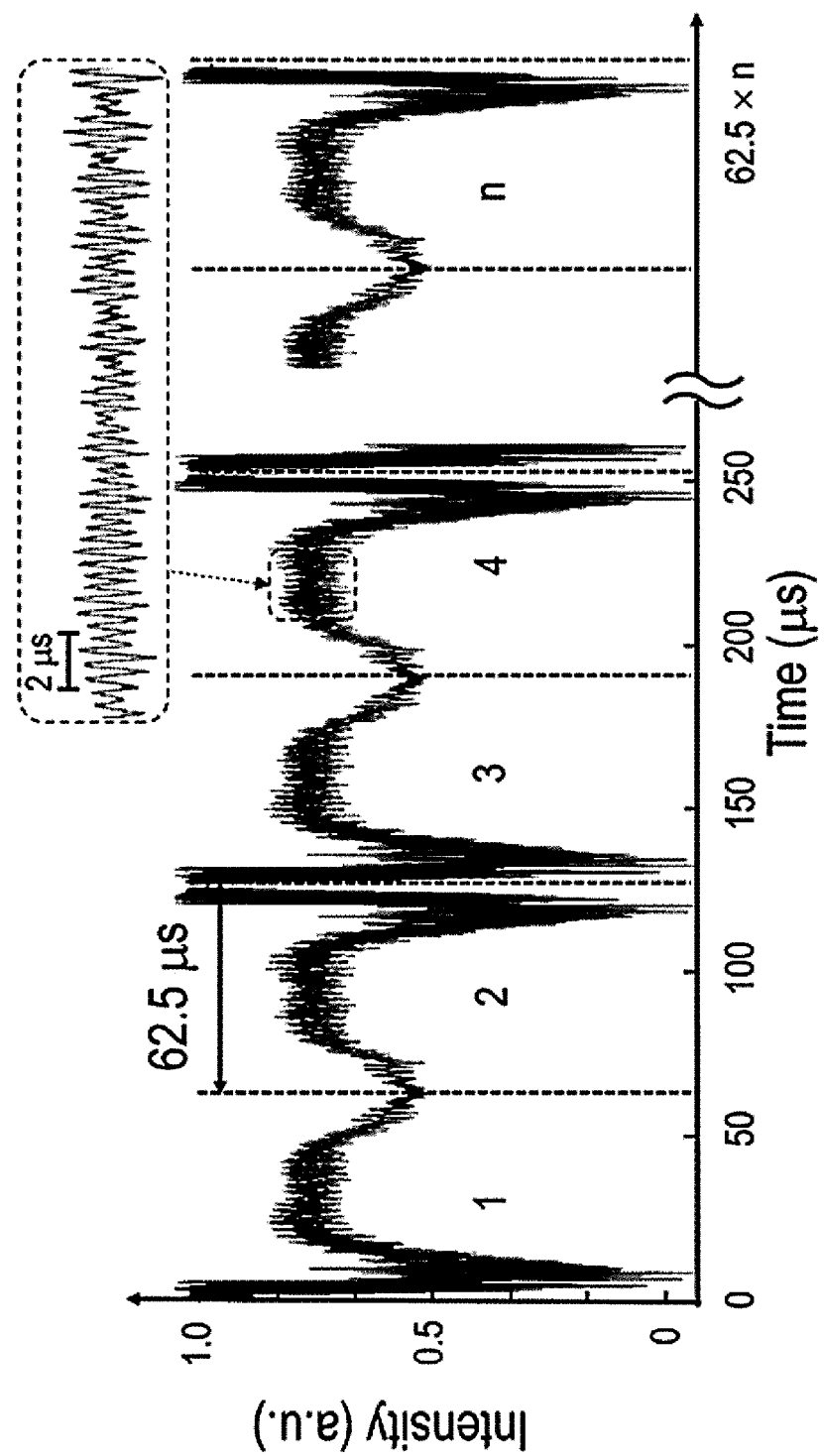
FIG. 6 is a graph showing an interferogram produced at the time of acquiring a molecular vibration spectrum of liquid toluene by using the Fourier transform-type spectroscopic device according to the embodiment of the present invention.
Figure 7:
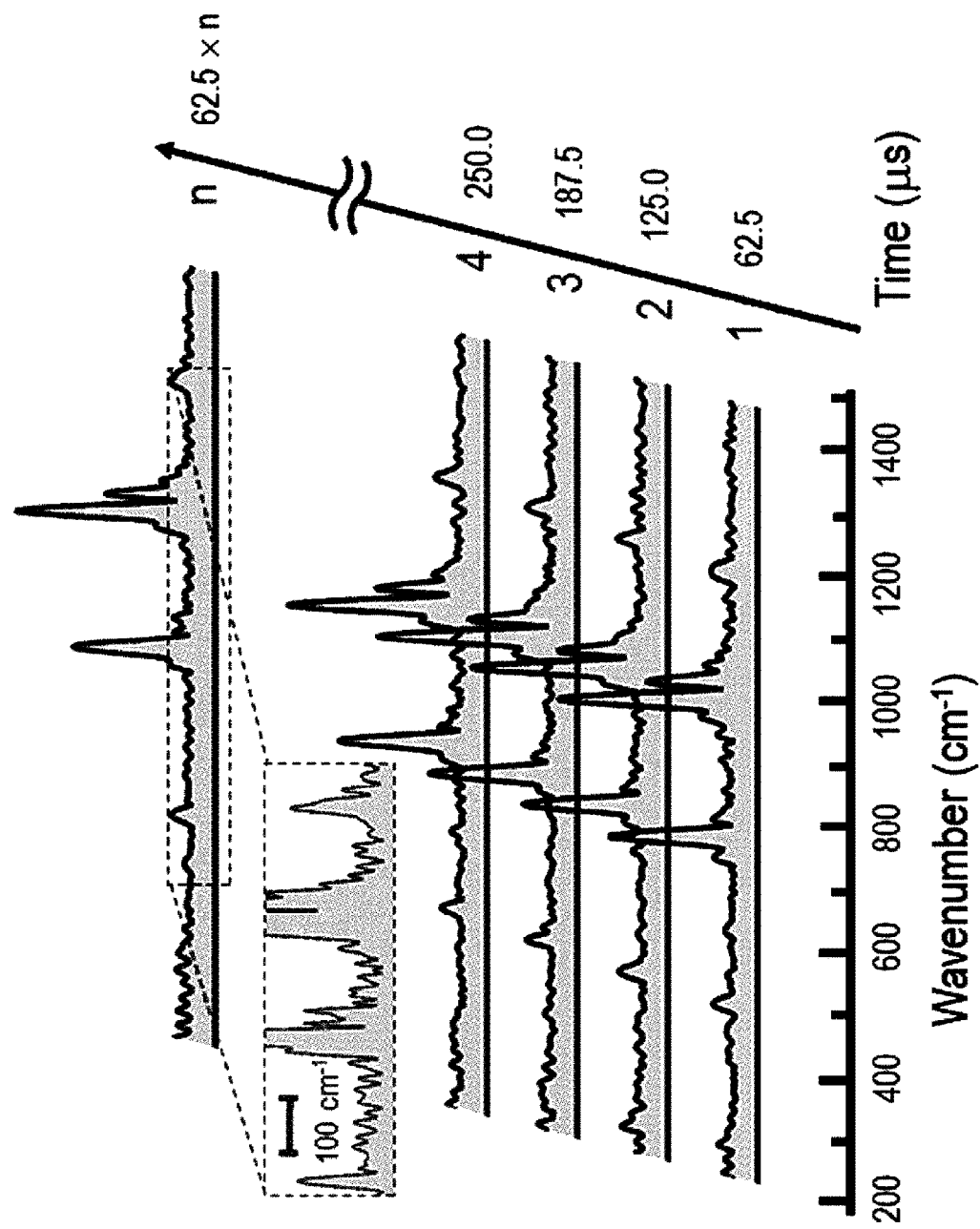
FIG. 7 is a molecular vibration spectrum of liquid toluene, obtained from the interferogram of FIG. 6.

As a verification test, a molecular vibration spectrum of liquid toluene was acquired using the Fourier transform-type spectroscopic device 1 of the above embodiment. FIG. 6 shows an interferogram of the anti-Stokes light 15 which was produced at the time of acquiring a molecular vibration spectrum, and FIG. 7 shows a molecular vibration spectrum obtained by performing a Fourier transform of the interferogram. In the interferogram of FIG. 6, a horizontal axis is a time axis (μs) and a vertical axis is relative intensity of the anti-Stokes light 15 detected by the photodetector 10. Each of numbers "1, 2, 3, . . . n" indicated in the interferogram corresponds to a number for each time of measurement of the molecular vibration spectrum in FIG. 7 and is provided for each interferogram for a half-period of a vibration period of the scanning mirror 26b. A horizontal axis in FIG. 7 is a wavenumber ($cm^{-1}$), and on the right side of FIG. 7, the number for each time of measurement of the molecular vibration spectrum and the measurement time are shown. FIG. 7 shows a plurality of molecular vibration spectra obtained by repeated measurement in order of the measurement time from the front. The molecular vibration spectrum represents relative intensity of anti-Stokes light for each wavenumber.

The scanning mirror 26b of the resonant scanner 26 in the Fourier transform-type spectroscopic device 1 vibrates at a frequency of 8 kHz and performs periodic motion at a frequency of 125 µs. Then, in the Fourier transform-type spectroscopic device 1, a molecular vibration spectrum can be obtained from each interferogram for a half-period, so that a molecular vibration spectrum can be obtained in every 62.5 µs. For this reason, FIG. 7 shows the time at intervals of 62.5 µs.

As shown in FIG. 7, in any of the acquired molecular vibration spectra, large peaks were observed in the vicinities of wavenumbers of 786 $cm^{-1}$, 1003 $cm^{-1}$, and 1031 $cm^{-1}$ in the molecular vibration peculiar to toluene. Further, as seen in an enlarged view of the molecular vibration spectrum shown in FIG. 7, small peaks were observed in the vicinities of wavenumbers of 522 $cm^{-1}$ and 1212 $cm^{-1}$ in the molecular vibration peculiar to toluene.

As thus described, it was confirmed that the molecular vibration spectrum can be acquired using the Fourier transform-type spectroscopic device 1 according to the embodiment of the present invention. It was thus confirmed that with the Fourier transform-type spectroscopic device 1, one molecular vibration spectrum can be acquired for each 62.5 µs, as many as 16,000 molecular vibration spectra can be acquired in one second, and the acquisition speed of the molecular vibration spectrum can be improved more than in the conventional case.

Figure 8:
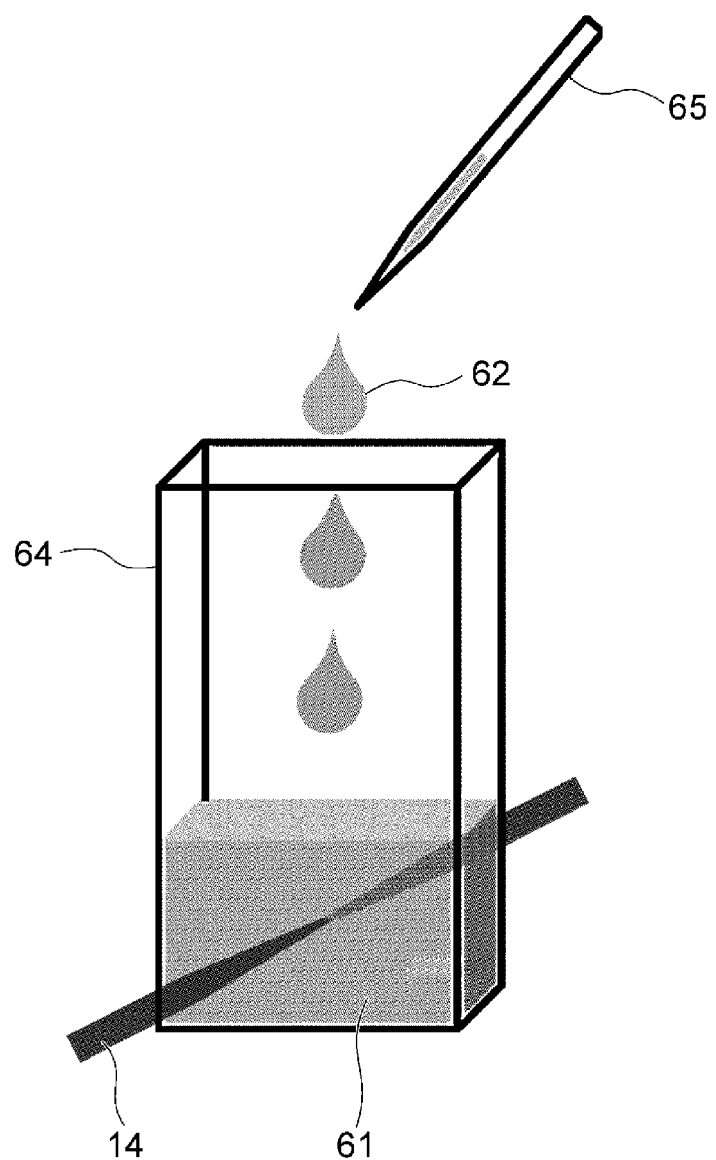
FIG. 8 is an explanatory view showing a measuring state at the time of measuring a change in a mixed state of liquid toluene and liquid benzene by using the Fourier transform-type spectroscopic device according to the embodiment of the present invention.
Figure 9A:
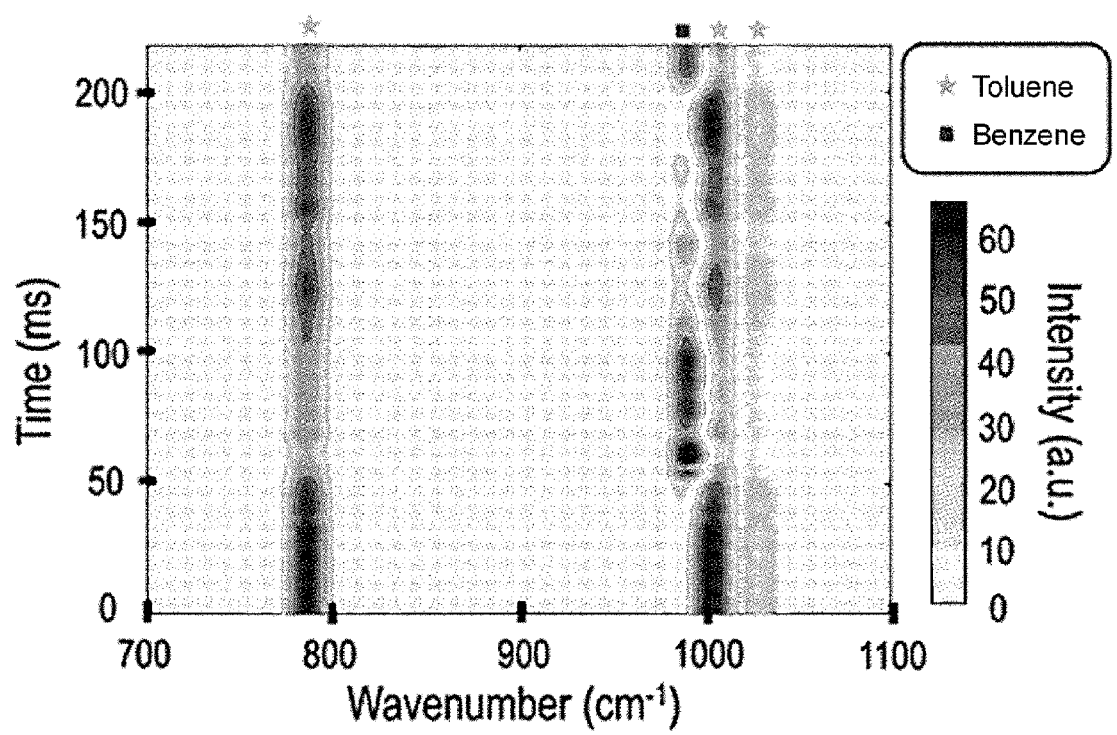
FIG. 9A is a graph showing a temporal change in a molecular vibration spectrum obtained by measuring the change in the mixed state.
Figure 9B:
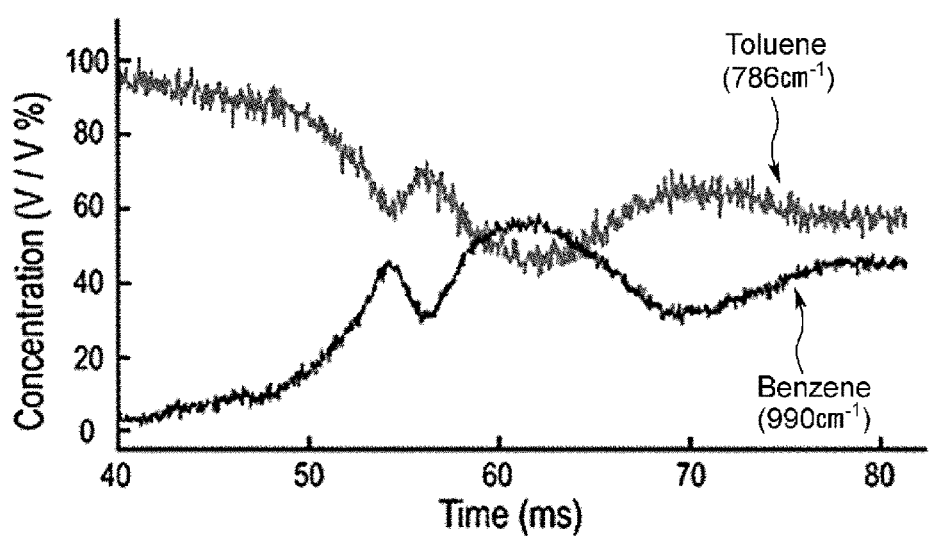
FIG. 9B is a graph showing a temporal change in a concentration of each liquid obtained from the temporal change in the molecular vibration spectrum.

Next, as shown in FIG. 8, by using the Fourier transform-type spectroscopic device 1A, a temporal change in a mixed state of toluene 61 and benzene 62 was measured as a change in the molecular vibration spectrum. In this measurement, a cuvette 64 with toluene 61 put therein was disposed between the first objective lens 6 and the second objective lens 8, and adjustment was made such that a focal point of the interference wave 14 (a focal position of the first objective lens 6) was in the cuvette 64 and the liquid in the cuvette 64 was irradiated with the interference wave 14. A plurality of drops of benzene 62 were put into the toluene 61 in the cuvette 64 from a pipette 65 to start measurement by the Fourier transform-type spectroscopic device 1A. FIGS. 9A and 9B show results of the measurement.

FIG. 9A shows a temporal change in the molecular vibration spectrum, in which a vertical axis is a time axis (ms) and a horizontal axis is a wavenumber ($cm^{-1}$). As shown in FIG. 9A, from the start of measurement, large peaks appeared in the vicinities of wavenumbers of 786 $cm^{-1}$, 1003 $cm^{-1}$, and 1031 $cm^{-1}$ in the molecular vibration peculiar to the toluene 61, and from the point in time at which about 40 ms has elapsed from the start of measurement, a peak appeared at a wavenumber of 990 $cm^{-1}$ in the molecular vibration peculiar to the benzene 62. It was observed that, when the peak at the wavenumber of the molecular vibration peculiar to the benzene 62 is strengthened, the peak at the wavenumber of the molecular vibration peculiar to the toluene 61 is weakened as contrary to the above.

The graph shown in FIG. 9B represents temporal changes in concentrations of the toluene 61 and the benzene 62 in measurement positions, in which a horizontal axis is a time axis (ms) and a vertical axis is the concentrations of the toluene 61 and the benzene 62. The temporal changes in the concentrations of the toluene 61 and the benzene 62 were obtained from the measured temporal change in the molecular vibration spectrum. That is, the concentration of the toluene 61 was converted from the intensity of the peak (the wavenumber of 786 $cm^{-1}$) of the toluene 61, and the concentration of the benzene 62 was converted from the intensity of the peak (the wavenumber of 990 $cm^{-1}$) of the benzene 62. As thus described, the Fourier transform-type spectroscopic device 1 has been improved in the acquisition speed of the molecular vibration spectrum, and it was thus confirmed that the Fourier transform-type spectroscopic device 1 is also suitable for observation of a state that changes in a short time.

Figure 10A:
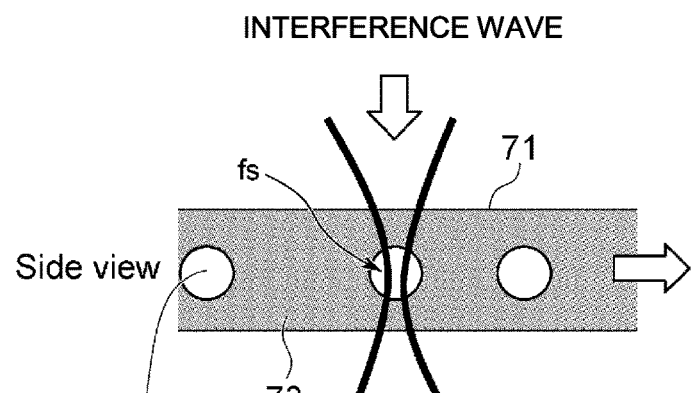
FIG. 10A is a side view of the micro flow path.
Figure 10B:
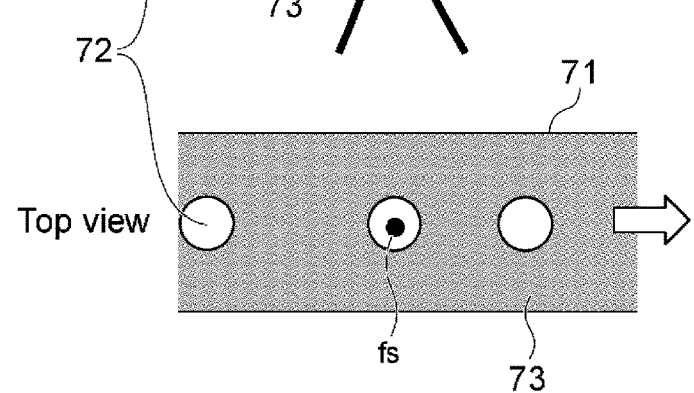
FIG. 10B is a top view seen of the micro flow path.

Further, the applicability of the Fourier transform-type spectroscopic device to flow cytometry was verified. In this verification, the Fourier transform-type spectroscopic device 1A was used. In FIGS. 10A and 10B, the position of a micro flow path 71 formed in a micro fluid device (now shown) was adjusted such that the micro flow path 71 was irradiated with the interference wave 14 from above and a focal point fs of the interference wave 14 was located almost at a vertical center of the micro flow path 71 as shown in FIG. 10A, and the focal point fs of the interference wave 14 was located almost at a widthwise (horizontal) center of the micro flow path 71 as shown in FIG. 10B. A plurality of beads 72 were allowed to flow with water 73 in the micro flow path 71 to measure a molecular vibration spectrum. Note that a diameter of the interference wave 14 at the focal point fs was 2.1 µm. The bead 72 was made of polystyrene with an average diameter of 16 µm and was allowed to flow in the micro flow path 71 at a flow rate of 0.04 m/s.

Figure 11A:
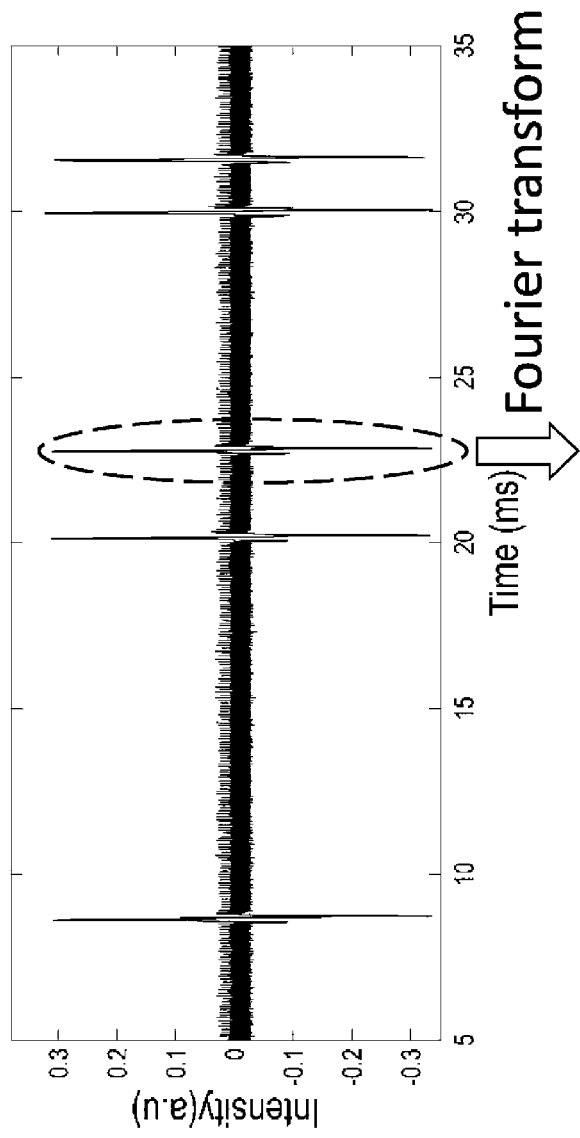
FIG. 11A is an interferogram produced at the time of measuring beads flowing in the micro flow path.
Figure 11B:
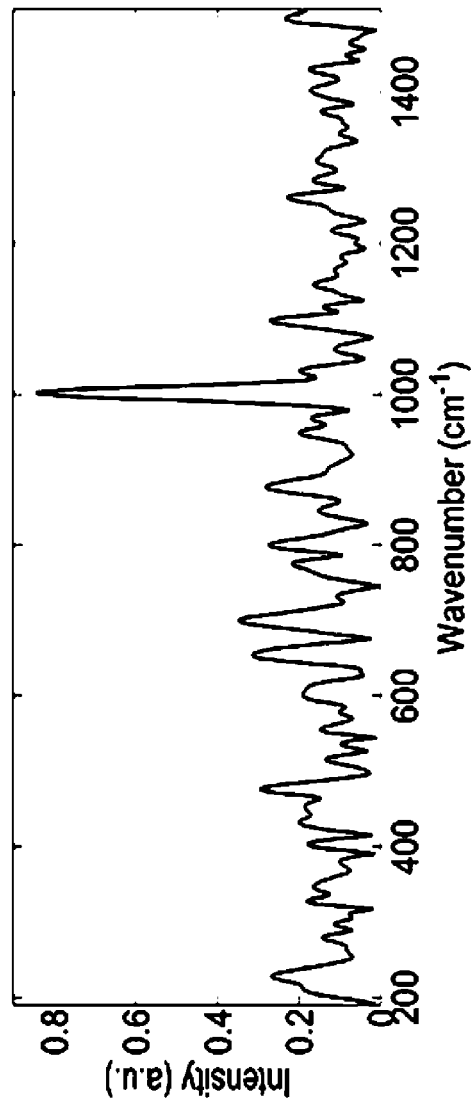
FIG. 11B is a molecular vibration spectrum obtained from the interferogram.

As shown in the produced interferogram of FIG. 11A, the anti-Stokes light 15 was detected each time the bead passed through the focal point fs of the interference wave 14, and a Fourier transform was performed on a portion of the interferogram where the anti-Stokes light 15 was detected to obtain a molecular vibration spectrum shown in FIG. 11B. In this obtained molecular vibration spectrum, a peak at a wavenumber of the molecular vibration peculiar to polystyrene was confirmed. In the interferogram of FIG. 11A, a horizontal axis is a time axis (ms) and a vertical axis is relative intensity of the anti-Stokes light 15 detected by the photodetector 10. In FIG. 11B, a horizontal axis is a wavenumber ($cm^{-1}$) and a vertical axis is relative intensity of the anti-Stokes light 15.

It was found from the above results that, because the Fourier transform-type spectroscopic device 1A repeatedly produces an interferogram at a high speed by using periodic motion due to the resonant vibration of the scanning mirror 26b, even when the sample such as the beads 72 pass through the focal point fs of the interference wave 14 in a short time and the timing for the passage is irregular, the molecular vibration spectrum of the sample can be acquired reliably, and it was thus confirmed that the Fourier transform-type spectroscopic device 1A is suitable for flow cytometry.

REFERENCE SIGNS LIST 1, 1A, 1B, 1D Fourier transform-type spectroscopic device
2 light source
3, 3A, 3B, 3D interferometer
4 compensator
7 sample
10 photodetector
12 PC
21, 21A, 21B, 21D first arm
22, 22A, 22B, 22C, 22D second arm 23 beam splitter
25, 34 first mirror
26, 42 resonant scanner
26b, 38b, 42b scanning mirror
28, 35, 43 second mirror
36, 40 diffractive optical element
38 polygon scanner

The invention claimed is:

1. A Fourier transform-type spectroscopic device comprising:
   an interferometer that includes a beam splitter which is configured to split light emitted from a light source into reference light and scanning light, a first arm which is configured to cause the reference light to be reflected on a first mirror and incident again on the beam splitter, and a second arm which is configured to cause the scanning light to be reflected on a second mirror and incident again on the beam splitter, the interferometer being configured to combine the reference light and the scanning light incident again on the beam splitter, to produce an interference wave;
   a photodetector that is configured to detect intensity of a plurality of beams of light, emitted from a sample that is repeatedly irradiated with the interference wave; and
   a computing device that is connected to the photodetector and is configured to produce an interferogram based on the intensity of the plurality of beams of light, and perform a Fourier transform of the interferogram,
   wherein the second arm includes a scanning mirror disposed on a light path of the scanning light between the beam splitter and the second mirror, and is configured to delay or advance the scanning light with respect to the reference light in accordance with a rotation angle of the scanning mirror from an initial position.

2. The Fourier transform-type spectroscopic device according to claim 1, comprising a compensator that is configured to compensate group velocity dispersion of the interference wave.

3. The Fourier transform-type spectroscopic device according to claim 1, wherein
   the second arm includes a collector lens that is configured to collect the scanning light on the scanning mirror, and
   the first arm includes a dispersion lens on a light path of the reference light between the beam splitter and the first mirror, the dispersion lens configured to cause occurrence of group velocity dispersion in the reference light which is group velocity dispersion caused to occur in the scanning light by the collector lens.

4. The Fourier transform-type spectroscopic device according to claim 1, wherein
   the second arm includes a diffractive optical element that is provided on a light path of the scanning light between the beam splitter and the scanning mirror and is configured to diffract the scanning light, and
   the second arm is configured to make a difference in a light path length among light beams with respective wavelength components of the scanning light in accordance with rotation angles of the scanning mirror from the initial position and vary a phase state of each of the light beams with the wavelength components in the scanning light, to delay or advance the scanning light with respect to the reference light.

5. The Fourier transform-type spectroscopic device according to claim 4, wherein the scanning mirror is provided on each side surface of a rotator in a shape of a polygonal pillar that is rotatable around a rotating shaft.

6. The Fourier transform-type spectroscopic device according to claim 1, wherein the scanning mirror is configured to perform periodic motion by resonance vibration.

7. The Fourier transform-type spectroscopic device according to claim 1, wherein each of the plurality of beams of light, emitted from the sample, is scattered light emitted due to coherent Raman scattering that occurs in the sample by irradiation with the interference wave.

8. The Fourier transform-type spectroscopic device according to claim 1, wherein each of the plurality of beams of light, emitted from the sample, is transmitted light or reflected light.

* * * * *